US010036741B2

(12) United States Patent
Mills et al.

(10) Patent No.: US 10,036,741 B2
(45) Date of Patent: Jul. 31, 2018

(54) SYSTEMS, MODELS AND METHODS FOR IDENTIFYING AND EVALUATING SKIN-ACTIVE AGENTS EFFECTIVE FOR TREATING AN ARRAY OF SKIN DISORDERS

(71) Applicant: The Procter & Gamble Company, Cincinnati, OH (US)

(72) Inventors: Kevin John Mills, Goshen, OH (US); Jun Xu, Mason, OH (US); Robert Lloyd Binder, Montgomery, OH (US); Robert Scott Youngquist, Mason, OH (US); Deborah Ruth Finlay, Cincinnati, OH (US); Charles Carson Bascom, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1310 days.

(21) Appl. No.: 13/966,418

(22) Filed: Aug. 14, 2013

(65) Prior Publication Data
US 2017/0343534 A1 Nov. 30, 2017

Related U.S. Application Data

(60) Provisional application No. 61/683,667, filed on Aug. 15, 2012.

(51) Int. Cl.
*G01N 33/48* (2006.01)
*G01N 33/50* (2006.01)
*G06F 17/30* (2006.01)

(52) U.S. Cl.
CPC ....... *G01N 33/502* (2013.01); *G01N 33/5008* (2013.01); *G06F 17/30424* (2013.01)

(58) Field of Classification Search
CPC .................................................. G01N 33/502
USPC ......................................................... 702/19
See application file for complete search history.

(56) References Cited

U.S. PATENT DOCUMENTS

| | | |
|---|---|---|
| 2,694,668 A | 11/1954 | Fricke |
| 2,809,971 A | 10/1957 | Bernstein |
| 2,826,551 A | 3/1958 | Geen |
| 3,152,046 A | 10/1964 | Kapral |
| 3,236,733 A | 2/1966 | Karsten |
| 3,753,196 A | 8/1973 | Kurtz |
| 3,755,560 A | 8/1973 | Dickert et al. |
| 3,761,418 A | 9/1973 | Parran |
| 3,964,500 A | 6/1976 | Drakoff |
| 4,323,683 A | 4/1982 | Bolich, Jr. |
| 4,345,080 A | 8/1982 | Bolich, Jr. |
| 4,364,837 A | 12/1982 | Pader |
| 4,379,753 A | 4/1983 | Bolich, Jr. |
| 4,421,769 A | 12/1983 | Dixon et al. |
| 4,470,982 A | 9/1984 | Winkler |
| 4,677,120 A | 6/1987 | Parish et al. |
| 4,741,855 A | 5/1988 | Grote |
| 4,885,107 A | 12/1989 | Wetzel |
| 4,885,311 A | 12/1989 | Parish et al. |
| 5,049,584 A | 9/1991 | Purcell et al. |
| 5,104,646 A | 4/1992 | Bolich, Jr. |
| 5,106,609 A | 4/1992 | Bolich, Jr. |
| 5,124,356 A | 6/1992 | Purcell et al. |
| RE34,075 E | 9/1992 | Purcell et al. |
| RE34,584 E | 4/1994 | Grote |
| 5,624,666 A | 4/1997 | Coffindaffer |
| 6,451,300 B1 | 9/2002 | Dunlop |
| 6,974,569 B2 | 12/2005 | Dunlop |
| 7,001,594 B1 | 2/2006 | Peffly |
| 7,101,889 B2 | 9/2006 | Kaczvinsky |
| 7,531,497 B2 | 5/2009 | Midha |
| 7,585,827 B2 | 9/2009 | Geary |
| 7,704,932 B2 | 4/2010 | Evans |
| 7,709,015 B2 | 5/2010 | Masuda |
| 7,727,516 B2 | 6/2010 | Botchkareva |
| 7,772,214 B2 | 8/2010 | Vatter |
| 2002/0044953 A1 | 4/2002 | Michelet et al. |
| 2002/0169562 A1 | 11/2002 | Stephanopoulos |
| 2003/0088437 A1 | 5/2003 | Iobst et al. |
| 2003/0223951 A1 | 12/2003 | Geary |
| 2007/0040306 A1 | 2/2007 | Morel et al. |
| 2007/0205226 A1 | 9/2007 | Honda et al. |
| 2009/0017080 A1 | 1/2009 | Tanner et al. |
| 2011/0150798 A1 | 6/2011 | Bacus |
| 2011/0269852 A1 | 11/2011 | McDaniel |
| 2012/0283112 A1 | 11/2012 | Binder |
| 2013/0259816 A1 | 10/2013 | Hakozaki et al. |

(Continued)

FOREIGN PATENT DOCUMENTS

| | | |
|---|---|---|
| GB | 849433 A | 9/1960 |
| JP | 2010-096748 | 4/2010 |

(Continued)

OTHER PUBLICATIONS

Millikin, Cheri et al. "Topical N-acetyl glucosamine and niacinamide affect pigmentation relevant gene expression in in vitro geonomics experimentation" Journal American Acadamy of Dermatology, Feb. 2007.
Bissett, Donald, et al. "Genomic Expression Changes Induced by Topical N-acetyl Glucosamine in Skin Equivalent Cultures in Vitro" Journal of Cosmetic Dermatology.
Yumiko, I., et al. "Identification of Novel Hair-Growth Inducers by means of Connectivity Mapping", FASEB Journal, vol. 24, May 2010.

(Continued)

Primary Examiner — Jerry Lin
(74) Attorney, Agent, or Firm — John G. Powell

(57) ABSTRACT

Methods and systems for constructing a gene expression signature representative of a number of biological conditions, systems and methods for determining functional relationships between a skin-active agent and skin conditions of interest, and methods and systems for identifying skin-active agents with broad spectrum activity are provided.

16 Claims, 18 Drawing Sheets

(56) References Cited

U.S. PATENT DOCUMENTS

| | | | |
|---|---|---|---|
| 2013/0261006 | A1 | 10/2013 | Hakozaki et al. |
| 2013/0261007 | A1 | 10/2013 | Hakozaki et al. |
| 2013/0261024 | A1 | 10/2013 | Hakozaki et al. |

FOREIGN PATENT DOCUMENTS

| | | |
|---|---|---|
| JP | 2010-099015 | 5/2010 |
| JP | 2011-122959 | 6/2011 |
| WO | WO 2003/100557 | 12/2003 |
| WO | WO 2005/040416 | 5/2005 |
| WO | WO 2007/077257 A2 | 7/2007 |
| WO | WO 2011/127150 A2 | 10/2011 |
| WO | WO 2011/133538 A1 | 10/2011 |
| WO | WO 2011/146768 A1 | 11/2011 |
| WO | 2012011904 A1 | 1/2012 |
| WO | 2012116081 A2 | 8/2012 |
| WO | WO 2012/135651 A1 | 10/2012 |
| WO | WO 2014/028572 | 2/2014 |

OTHER PUBLICATIONS

Hughes, T.R. et al. "Functional discovery via a compendium of expression profiles" Cell vol. 102, 109-126 (2000).
Jagetia G. C. et al, "Genotoxic Effect of Hydroquinone on the Cultured Mouse Spleenocytes"Toxicology Letter 121(1):15-20, 2001.
Lamb, Justin, et al. "Connectivity Map: Gene Expression Signatures to Connect Small Molecules, Genes, and Disease", Science, vol. 313, 2006.
M. Hollander et al. "Nonparametric Statistical Methods"; Wiley, New York, ed. 2, 1999 see, e.g., pp. 178-185.
Raynaud E. et al., "Depigmentation for cosmetic purposes: prevalence and side-effects in a female population in Senegal "Ann Dermatol Venereol 128(6-7):720-724, 2001 (abstract).
Shimizu K. et al., "The skin-lightening effects of artocarpin on UVB-induced pigmentation "Planta Med 68(1):79-81, 2002.
Sivapirabu, G. et al., "Topical Nicotinamide Modulates Cellular Energy Metabolism and Provides Broad-Spectrum Protection Against Ultraviolet Radiation-Induced Immunosuppression in Humans", British Journal of Dermatology 2009.
Subramanian A. et al, Gene set enrichment analysis: A knowledge-based approach for interpreting genome-wide expression profiles. (2005) Proc.Natl.Acad Sci U.S.A, 102, 15545-15550.
International Search Report; PCT/US2013/034055; dated Jun. 11, 2013; 17 pages.
International Search Report PCT/US2013/034052; dated Jun. 11, 2013; 18 pages.
International Search Report PCT/US2013/034054; dated Jun. 13, 2013; 18 pages.
International Search Report PCT/US2013/034055; dated Jun. 11, 2013; 17 pages.
International Search Report PCT/US2013/034117; dated Jun. 11, 2013; 17 pages.
Johnson, "Skin conditions and related need for medical care amount persons 1-74 years, United States, 1971-1974." Vital and Health Statistics, Series 11, No. 212, DHEW publication No. (PHS) 79-1660, U.S. Department of Health, Education and Welfare, National Center for Health Statistics 1978: 1-72.
Smith et al.,"The effect of a high-protein, low glycemic-load diet versus a conventional, high glycemic-load diet on biochemical parameters associated with acne vulgaris: a randomized, investigator-masked, controlled trial" Journal of the American Academy of Dermatology vol. 57 (2): 247-56 (2007).
Kluken et al., "Atopic eczema/dermatitis syndrome—a genetically complex disease. New advances in discovering the genetic contribution" Allergy, 58(1):5-12 (2003).
Cork et al., "Epidermal barrier dysfunction in atopic dermatitis" J Invest Dermatol., 129(8):1892-908 (2009).

Kimata et al., "Enhancement of Allergic Skin Wheal Responses by Microwave Radiation from Mobile Phones in Patients with Atopic Eczema/Dermatitis Syndrome" Int Arch of Allergy and Immunology, 129 (4):348-350 (2002).
Wang et al., "Environmental risk factors for early infantile atopic dermatitis" Pediatr Allergy Immunol., 18(5):441-7 (2007).
Hughes, Timothy et al. "Functional discovery via a compendium of expression profiles" Cell vol. 102, 2000, pp. 109-126.
Lamb, Justin, et al. "Connectivity Map: Gene Expression Signatures to Connect Small Molecules, Genes, and Disease," Science, vol. 313, 2006; 8 pages.
Bier et al., "DNA Microarrays" Adv. Biochem. Eng. Biotechnol., 109:433-53 (2008).
Hoheisel, "Microarray Technology: Beyond Transcript Profiling and Genotype Analysis" Nat. Rev. Genet., 7:200-10 (2006).
Fan et al., "Illumina universal bead arrays" Methods Enzymol., 410:57-73 (2006).
Raqoussis & Elvidger, "Affymetrix GeneChip system: moving from research to the Clinic" Expert Rev. Mol. Diagn., 6:145-52 (2006).
Mockler et al., "Applications of DNA tiling arrays for whole-genome analysis" Genomics, 85:1-15 (2005).
Hollander, M. et al. "Nonparametric Statistical Methods"; Wiley, New York, ed. 2, 1999 pp. 178-185.
Lamb et al. "Gene Set Enrichment Analysis: A Knowledge Based Approach for Interpreting Genome-wide Expression profiles", Proc. Natl.Acad Sci U.S.A, 102, 15545-15550.
Trivedi, N. et al., "Gene array expression profiling in acne lesions reveals marked upregulation of genes involved in inflammation and matrix remodeling," J Invest Dermatol;126(5):1071-9 (2006).
Plager, D. et al. "Early cutaneous gene transcription changes in adult atopic dermatitis and potential clinical implications," Exp Dermatol;16(1):28-36 (2007).
Olsson, M. et al. "Increased expression of aquaporin 3 in atopic eczema," Allergy; 61(9):1132-7.
Mobini, R. et al. "A module-based analytical strategy to identify novel disease-associated genes shows an inhibitory role for interleukin 7 Receptor in allergic inflammation," BMC Syst Biol; 3:19 (2009).
Nair et al., "Genome-wide scan reveals association of psoriasis with IL-23 and NF-kappaB pathways," Nat Genet; 41(2):199-204(2009).
Swindell et al., "Genome-wide expression profiling of five mouse models identifies similarities and differences with human psoriasis," PLoS One; 6(4); Apr. 2011; 20 pages.
Mills, K.J. "Dandruff/seborrhoeic dermatitis is characterized by an inflammatory genomic signature and possible immune dysfunction" Transcriptional Analysis of the condition and treatment effects of zinc pyrithione 2012 British Association of Dermatologists 166 (Suppl 2), pp. 33-40.
Mihaly, J. "Decreased retinoid concentration and retinoid signaling pathways in human atopic dermatitis" 2011 John Wiley & Sons, Experimental Dermatology, 20, pp. 326-330.
Ding-Dar, L. "Retinoid-Responsive Trascriptional Changes in Epidermal Keratinocytes" J. Cellular Physiology 220: pp. 427-329; 2009.
Guttman-Yassky E., et al., "Major differences in inflammatory dendritic cells and their products distinguish atopic dermatitis from psoriasis", J. Allergy Clin. Immunol., vol. 119, No. 5, pp. 1210-1217, May 2007, USA.
Bhogal et al., Toxicity Testing: creating a revolution based on new technologies, TRENDS in Biotechnology, vol. 23, No. 6, Jun. 2005, pp. 299-307.
De Magalhães, Ageing research in the post-genome era: New technologies for an old problem, pp. 99-115 in Redox Metabolism and Longevity Relationships in Animals and Plants, vol. 62, Feb. 2009.
International Search Report and Written Opinion of the International Searching Authority dated Oct. 30, 2013, PCT/US2013/054855, 10 pages.
International Search Report and Written Opinion of the International Searching Authority dated Oct. 28, 2013, PCT/US2013/054857, 12 pages.

(56) References Cited

OTHER PUBLICATIONS

International Search Report and Written Opinion of the International Searching Authority dated Apr. 4, 2014, PCT/US2013/054861, 15 pages.
Lamb, The Connectivity Map: a new tool for biomedical research, NATURE REVIEWSlCANCER, Nature Publishing Group, vol. 7, Jan. 2007, pp. 54-60.
Mills et al., Transcriptomic Profiling Reveals New Insights Into The Pathogenesis Of Dandruff/Seborrheic Dermatitis And The Efficacy Of ZPT, $22^{nd}$ World Congress of Dermatology, May 24, 2011.
Vertuani et al., Determination of antioxidant efficacy of cosmetic formulations by non-invasive measurements, Skin Research and Technology, vol. 9, No. 3, Aug. 2003, pp. 245-253.
U.S. Appl. No. 13/851,858, filed Mar. 27, 2013, Hakozaki.
U.S. Appl. No. 13/851,864, filed Mar. 27, 2013, Hakozaki.
U.S. Appl. No. 13/851,873, filed Mar. 27, 2013, Hakozaki.
U.S. Appl. No. 13/851,886, filed Mar. 27, 2013, Hakozaki.

FIG. 1A

| Affymetrix Probe Id | Gene Symbol | Consistency Score | Description |
|---|---|---|---|
| 201644_at | TSTA3 | 4.892 | tissue specific transplantation antigen P35B |
| 36936_at | TSTA3 | 4.892 | tissue specific transplantation antigen P35B |
| 205325_at | PHYHIP | -4.887 | phytanoyl-CoA 2-hydroxylase interacting protein |
| 221249_s_at | FAM117A | -4.886 | family with sequence similarity 117, member A |
| 202976_s_at | RHOBTB3 | -4.86 | Rho-related BTB domain containing 3 |
| 204589_at | NUAK1 | -4.856 | NUAK family, SNF1-like kinase, 1 |
| 206149_at | CHP2 | -4.852 | calcineurin B homologous protein 2 |
| 220966_x_at | ARPC5L | 4.834 | actin related protein 2/3 complex, subunit 5-like |
| 218820_at | C14orf132 | -4.832 | chromosome 14 open reading frame 132 |
| 218528_s_at | RNF38 | -4.821 | ring finger protein 38 |
| 217834_s_at | SYNCRIP | 4.807 | synaptotagmin binding, cytoplasmic RNA interacting protein |
| 221834_at | LONP2 | -4.794 | lon peptidase 2, peroxisomal |
| 201594_s_at | PPP4R1 | 4.793 | protein phosphatase 4, regulatory subunit 1 |
| 214226_at | POL3S | 4.787 | polyserase 3 |
| 209191_at | TUBB6 | 4.785 | tubulin, beta 6 |
| 208696_at | CCT5 | 4.781 | chaperonin containing TCP1, subunit 5 (epsilon) |
| 219956_at | GALNT6 | 4.773 | UDP-N-acetyl-alpha-D-galactosamine:polypeptide N-acetylgalactosaminyltransferase 6 (GalNAc-T6) |
| 222362_at | 222362_at | -4.771 | 222362_at |
| 219099_at | C12orf5 | 4.77 | chromosome 12 open reading frame 5 |
| 208540_x_at | S100A11P | 4.765 | S100 calcium binding protein A11 pseudogene |
| 218335_x_at | TNIP2 | 4.749 | TNFAIP3 interacting protein 2 |
| 217106_x_at | DIMT1L | 4.748 | DIM1 dimethyladenosine transferase 1-like (S. cerevisiae) |
| 208655_at | CCNI | -4.738 | cyclin I |
| 219132_at | PELI2 | -4.735 | pellino homolog 2 (Drosophila) |
| 201245_s_at | OTUB1 | 4.728 | OTU domain, ubiquitin aldehyde binding 1 |
| 203766_s_at | LMOD1 | -4.724 | leiomodin 1 (smooth muscle) |
| 203779_s_at | MPZL2 | 4.722 | myelin protein zero-like 2 |
| 212510_at | GPD1L | -4.721 | glycerol-3-phosphate dehydrogenase 1-like |
| 201584_s_at | DDX39 | 4.715 | DEAD (Asp-Glu-Ala-Asp) box polypeptide 39 |
| 215945_s_at | TRIM2 | -4.711 | tripartite motif-containing 2 |
| 210213_s_at | EIF6 | 4.708 | eukaryotic translation initiation factor 6 |

FIG. 1B

| | | | |
|---|---|---|---|
| 56197_at | PLSCR3 | 4.705 | phospholipid scramblase 3 |
| 201721_s_at | LAPTM5 | 4.698 | lysosomal associated multispanning membrane protein 5 |
| 203780_at | MPZL2 | 4.692 | myelin protein zero-like 2 |
| 220330_s_at | SAMSN1 | 4.68 | SAM domain, SH3 domain and nuclear localization signals 1 |
| 210692_s_at | SLC43A3 | 4.663 | solute carrier family 43, member 3 |
| 201989_s_at | CREBL2 | -4.656 | cAMP responsive element binding protein-like 2 |
| 219440_at | RAI2 | -4.655 | retinoic acid induced 2 |
| 217897_at | FXYD6 | -4.642 | FXYD domain containing ion transport regulator 6 |
| 204026_s_at | ZWINT | 4.63 | ZW10 interactor |
| 221755_at | EHBP1L1 | 4.628 | EH domain binding protein 1-like 1 |
| 209733_at | MID2 | -4.626 | midline 2 |
| 206015_s_at | FOXJ3 | -4.624 | forkhead box J3 |
| 203148_s_at | TRIM14 | 4.619 | tripartite motif-containing 14 |
| 205292_s_at | HNRNPA2B1 | 4.617 | heterogeneous nuclear ribonucleoprotein A2/B1 |
| 218418_s_at | ANKRD25 | -4.614 | ankyrin repeat domain 25 |
| 48531_at | TNIP2 | 4.609 | TNFAIP3 interacting protein 2 |
| 210111_s_at | KIAA0265 | -4.603 | KIAA0265 protein |
| 201323_at | EBNA1BP2 | 4.597 | EBNA1 binding protein 2 |
| 58780_s_at | FLJ10357 | -4.595 | hypothetical protein FLJ10357 |
| 208158_s_at | OSBPL1A | -4.582 | oxysterol binding protein-like 1A |
| 213716_s_at | SECTM1 | 4.556 | secreted and transmembrane 1 |
| 221601_s_at | FAIM3 | 4.549 | Fas apoptotic inhibitory molecule 3 |
| 32069_at | N4BP1 | 4.542 | Nedd4 binding protein 1 |
| 204601_at | N4BP1 | 4.541 | Nedd4 binding protein 1 |
| 202567_at | SNRPD3 | 4.541 | small nuclear ribonucleoprotein D3 polypeptide 18kDa |
| 201788_at | DDX42 | -4.535 | DEAD (Asp-Glu-Ala-Asp) box polypeptide 42 |
| 201720_s_at | LAPTM5 | 4.535 | lysosomal associated multispanning membrane protein 5 |
| 218546_at | C1orf115 | -4.531 | chromosome 1 open reading frame 115 |
| 216565_x_at | LOC391020 | 4.523 | interferon induced transmembrane protein pseudogene |
| 212875_s_at | C21orf25 | -4.514 | chromosome 21 open reading frame 25 |
| 208662_s_at | TTC3 | -4.513 | tetratricopeptide repeat domain 3 |
| 208646_at | RPS14 | -4.502 | ribosomal protein S14 |
| 221807_s_at | TRABD | 4.493 | TraB domain containing |
| 212498_at | 212498_at | -4.488 | 212498_at |

FIG. 1C

| 218448_at | C20orf11 | 4.464 | chromosome 20 open reading frame 11 |
|---|---|---|---|
| 221899_at | PFAAP5 | -4.463 | phosphonoformate immuno-associated protein 5 |
| 213122_at | TSPYL5 | -4.452 | TSPY-like 5 |
| 216952_s_at | 216952_s_at | 4.451 | 216952_s_at |
| 212970_at | 212970_at | -4.447 | 212970_at |
| 220755_s_at | C6orf48 | -4.425 | chromosome 6 open reading frame 48 |
| 218192_at | IHPK2 | -4.41 | inositol hexaphosphate kinase 2 |
| 207705_s_at | RP4-691N24.1 | -4.409 | KIAA0980 protein |
| 207168_s_at | H2AFY | 4.859 | H2A histone family, member Y |
| 218087_s_at | SORBS1 | -4.843 | sorbin and SH3 domain containing 1 |
| 217781_s_at | ZFP106 | -4.837 | zinc finger protein 106 homolog (mouse) |
| 204300_at | PET112L | 4.832 | PET112-like (yeast) |
| 205847_at | PRSS22 | 4.824 | protease, serine, 22 |
| 214501_s_at | H2AFY | 4.702 | H2A histone family, member Y |
| 217992_s_at | EFHD2 | 4.697 | EF-hand domain family, member D2 |
| 203964_at | NMI | 4.696 | N-myc (and STAT) interactor |
| 213900_at | C9orf61 | -4.623 | chromosome 9 open reading frame 61 |
| 213050_at | COBL | -4.618 | cordon-bleu homolog (mouse) |
| 209100_at | IFRD2 | 4.594 | interferon-related developmental regulator 2 |
| 212830_at | MEGF9 | -4.571 | multiple EGF-like-domains 9 |
| 213974_at | ADAMTSL3 | -4.565 | ADAMTS-like 3 |
| 219194_at | SEMA4G | -4.563 | sema domain, immunoglobulin domain (Ig), transmembrane domain (TM) and short cytoplasmic domain, (semaphorin) 4G |
| 220104_at | ZC3HAV1 | 4.558 | zinc finger CCCH-type, antiviral 1 |
| 203234_at | UPP1 | 4.557 | uridine phosphorylase 1 |
| 218637_at | IMPACT | -4.538 | Impact homolog (mouse) |
| 210212_x_at | MTCP1 | -4.513 | mature T-cell proliferation 1 |
| 206481_s_at | LDB2 | -4.498 | LIM domain binding 2 |
| 41037_at | TEAD4 | 4.498 | TEA domain family member 4 |
| 212805_at | PRUNE2 | -4.486 | prune homolog 2 (Drosophila) |
| 219329_s_at | C2orf28 | -4.482 | chromosome 2 open reading frame 28 |
| 218384_at | CARHSP1 | -4.479 | calcium regulated heat stable protein 1, 24kDa |
| 206932_at | CH25H | 4.448 | cholesterol 25-hydroxylase |
| 221987_s_at | TSR1 | 4.438 | TSR1, 20S rRNA accumulation, homolog (S. cerevisiae) |
| 204166_at | SBNO2 | 4.427 | strawberry notch homolog 2 (Drosophila) |
| 215028_at | SEMA6A | -4.408 | sema domain, transmembrane domain (TM), and |

FIG. 1D

| | | | |
|---|---|---|---|
| | | | cytoplasmic domain, (semaphorin) 6A |
| 201516_at | SRM | 4.407 | spermidine synthase |
| 208539_x_at | SPRR2D | 4.903 | small proline-rich protein 2D |
| 220658_s_at | ARNTL2 | 4.885 | aryl hydrocarbon receptor nuclear translocator-like 2 |
| 218471_s_at | BBS1 | -4.859 | Bardet-Biedl syndrome 1 |
| 220664_at | SPRR2C | 4.817 | small proline-rich protein 2C |
| 200734_s_at | ARF3 | 4.815 | ADP-ribosylation factor 3 |
| 205807_s_at | TUFT1 | -4.798 | tuftelin 1 |
| 213227_at | PGRMC2 | -4.775 | progesterone receptor membrane component 2 |
| 221476_s_at | RPL15 | -4.768 | ribosomal protein L15 |
| 209825_s_at | UCK2 | 4.762 | uridine-cytidine kinase 2 |
| 212321_at | SGPL1 | -4.73 | sphingosine-1-phosphate lyase 1 |
| 209417_s_at | IFI35 | 4.718 | interferon-induced protein 35 |
| 201701_s_at | PGRMC2 | -4.669 | progesterone receptor membrane component 2 |
| 209015_s_at | DNAJB6 | 4.666 | DnaJ (Hsp40) homolog, subfamily B, member 6 |
| 202747_s_at | ITM2A | -4.65 | integral membrane protein 2A |
| 201303_at | EIF4A3 | 4.648 | eukaryotic translation initiation factor 4A, isoform 3 |
| 203476_at | TPBG | 4.633 | trophoblast glycoprotein |
| 201762_s_at | PSME2 | 4.614 | proteasome (prosome, macropain) activator subunit 2 (PA28 beta) |
| 55081_at | MICALL1 | 4.603 | MICAL-like 1 |
| 204972_at | OAS2 | 4.6 | 2'-5'-oligoadenylate synthetase 2, 69/71kDa |
| 209546_s_at | APOL1 | 4.551 | apolipoprotein L, 1 |
| 202746_at | ITM2A | -4.545 | integral membrane protein 2A |
| 209509_s_at | DPAGT1 | 4.49 | dolichyl-phosphate (UDP-N-acetylglucosamine) N-acetylglucosaminephosphotransferase 1 (GlcNAc-1-P transferase) |
| 219202_at | RHBDF2 | 4.45 | rhomboid 5 homolog 2 (Drosophila) |
| 200810_s_at | CIRBP | -4.445 | cold inducible RNA binding protein |
| 204872_at | TLE4 | -4.864 | transducin-like enhancer of split 4 (E(sp1) homolog, Drosophila) |
| 205412_at | ACAT1 | -4.668 | acetyl-Coenzyme A acetyltransferase 1 (acetoacetyl Coenzyme A thiolase) |
| 215438_x_at | GSPT1 | 4.667 | G1 to S phase transition 1 |
| 201192_s_at | PITPNA | 4.662 | phosphatidylinositol transfer protein, alpha |
| 214793_at | DUSP7 | 4.6 | dual specificity phosphatase 7 |
| 218542_at | CEP55 | 4.584 | centrosomal protein 55kDa |
| 205241_at | SCO2 | 4.579 | SCO cytochrome oxidase deficient homolog 2 (yeast) |

FIG. 1E

| | | | |
|---|---|---|---|
| 202069_s_at | IDH3A | 4.559 | isocitrate dehydrogenase 3 (NAD+) alpha |
| 206445_s_at | PRMT1 | 4.557 | protein arginine methyltransferase 1 |
| 204020_at | PURA | -4.554 | purine-rich element binding protein A |
| 210138_at | RGS20 | 4.897 | regulator of G-protein signaling 20 |
| 208865_at | CSNK1A1 | 4.871 | casein kinase 1, alpha 1 |
| 213923_at | RAP2B | 4.771 | RAP2B, member of RAS oncogene family |
| 218960_at | TMPRSS4 | 4.765 | transmembrane protease, serine 4 |
| 213086_s_at | CSNK1A1 | 4.74 | casein kinase 1, alpha 1 |
| 217762_s_at | RAB31 | 4.737 | RAB31, member RAS oncogene family |
| 201954_at | ARPC1B | 4.703 | actin related protein 2/3 complex, subunit 1B, 41kDa |
| 218625_at | NRN1 | -4.699 | neuritin 1 |
| 213860_x_at | CSNK1A1 | 4.692 | casein kinase 1, alpha 1 |
| 211787_s_at | EIF4A1 | 4.687 | eukaryotic translation initiation factor 4A, isoform 1 |
| 217764_s_at | RAB31 | 4.664 | RAB31, member RAS oncogene family |
| 217763_s_at | RAB31 | 4.658 | RAB31, member RAS oncogene family |
| 219304_s_at | PDGFD | -4.641 | platelet derived growth factor D |
| 204170_s_at | CKS2 | 4.634 | CDC28 protein kinase regulatory subunit 2 |
| 221958_s_at | GPR177 | -4.617 | G protein-coupled receptor 177 |
| 208498_s_at | AMY1A | -4.572 | amylase, alpha 1A (salivary) |
| 201530_x_at | EIF4A1 | 4.543 | eukaryotic translation initiation factor 4A, isoform 1 |
| 200004_at | EIF4G2 | 4.422 | eukaryotic translation initiation factor 4 gamma, 2 |
| 209292_at | ID4 | -4.856 | inhibitor of DNA binding 4, dominant negative helix-loop-helix protein |
| 209291_at | ID4 | -4.748 | inhibitor of DNA binding 4, dominant negative helix-loop-helix protein |
| 202432_at | PPP3CB | -4.6 | protein phosphatase 3 (formerly 2B), catalytic subunit, beta isoform |
| 206499_s_at | RCC1 | 4.563 | regulator of chromosome condensation 1 |
| 202446_s_at | PLSCR1 | 4.563 | phospholipid scramblase 1 |
| 207121_s_at | MAPK6 | 4.541 | mitogen-activated protein kinase 6 |
| 212048_s_at | YARS | 4.481 | tyrosyl-tRNA synthetase |
| 220322_at | IL1F9 | 4.758 | interleukin 1 family, member 9 |
| 212071_s_at | SPTBN1 | -4.742 | spectrin, beta, non-erythrocytic 1 |
| 203296_s_at | ATP1A2 | -4.723 | ATPase, Na+/K+ transporting, alpha 2 (+) polypeptide |
| 205402_x_at | PRSS2 | 4.532 | protease, serine, 2 (trypsin 2) |
| 206628_at | SLC5A1 | 4.888 | solute carrier family 5 (sodium/glucose cotransporter), member 1 |
| 215235_at | SPTAN1 | -4.7 | spectrin, alpha, non-erythrocytic 1 (alpha-fodrin) |

FIG. 1F

| | | | |
|---|---|---|---|
| 209108_at | TSPAN6 | -4.68 | tetraspanin 6 |
| 203498_at | RCAN2 | -4.62 | regulator of calcineurin 2 |
| 209071_s_at | RGS5 | -4.62 | regulator of G-protein signaling 5 |
| 212508_at | MOAP1 | -4.607 | modulator of apoptosis 1 |
| 201853_s_at | CDC25B | 4.558 | cell division cycle 25 homolog B (S. pombe) |
| 201858_s_at | SRGN | 4.484 | serglycin |
| 214925_s_at | SPTAN1 | -4.444 | spectrin, alpha, non-erythrocytic 1 (alpha-fodrin) |
| 222062_at | IL27RA | 4.804 | interleukin 27 receptor, alpha |
| 201470_at | GSTO1 | 4.694 | glutathione S-transferase omega 1 |
| 212372_at | MYH10 | -4.656 | myosin, heavy chain 10, non-muscle |
| 201540_at | FHL1 | -4.533 | four and a half LIM domains 1 |
| 204632_at | RPS6KA4 | 4.511 | ribosomal protein S6 kinase, 90kDa, polypeptide 4 |
| 202659_at | PSMB10 | 4.444 | proteasome (prosome, macropain) subunit, beta type, 10 |
| 201890_at | RRM2 | 4.758 | ribonucleotide reductase M2 polypeptide |
| 203081_at | CTNNBIP1 | -4.703 | catenin, beta interacting protein 1 |
| 203824_at | TSPAN8 | -4.663 | tetraspanin 8 |
| 217388_s_at | KYNU | 4.608 | kynureninase (L-kynurenine hydrolase) |
| 206571_s_at | MAP4K4 | 4.584 | mitogen-activated protein kinase kinase kinase kinase 4 |
| 219630_at | PDZK1IP1 | 4.903 | PDZK1 interacting protein 1 |
| 221527_s_at | PARD3 | -4.832 | par-3 partitioning defective 3 homolog (C. elegans) |
| 202724_s_at | FOXO1 | -4.641 | forkhead box O1 |
| 204715_at | PANX1 | 4.812 | pannexin 1 |
| 201422_at | IFI30 | 4.773 | interferon, gamma-inducible protein 30 |
| 222125_s_at | PH-4 | -4.584 | hypoxia-inducible factor prolyl 4-hydroxylase |
| 203175_at | RHOG | 4.542 | ras homolog gene family, member G (rho G) |
| 203697_at | FRZB | -4.857 | frizzled-related protein |
| 203698_s_at | FRZB | -4.795 | frizzled-related protein |
| 217272_s_at | SERPINB13 | 4.655 | serpin peptidase inhibitor, clade B (ovalbumin), member 13 |
| 202350_s_at | MATN2 | -4.508 | matrilin 2 |
| 206503_x_at | PML | 4.479 | promyelocytic leukemia |
| 200650_s_at | LDHA | 4.566 | lactate dehydrogenase A |
| 205064_at | SPRR1B | 4.596 | small proline-rich protein 1B (cornifin) |
| 217755_at | HN1 | 4.833 | hematological and neurological expressed 1 |
| 204712_at | WIF1 | -4.639 | WNT inhibitory factor 1 |
| 202180_s_at | MVP | 4.593 | major vault protein |

FIG. 1G

| 204032_at | BCAR3 | -4.776 | breast cancer anti-estrogen resistance 3 |
|---|---|---|---|
| 204232_at | FCER1G | 4.574 | Fc fragment of IgE, high affinity I, receptor for; gamma polypeptide |
| 218856_at | TNFRSF21 | 4.534 | tumor necrosis factor receptor superfamily, member 21 |
| 206276_at | LY6D | 4.915 | lymphocyte antigen 6 complex, locus D |
| 201739_at | SGK | 4.895 | serum/glucocorticoid regulated kinase |
| 213706_at | GPD1 | -4.438 | glycerol-3-phosphate dehydrogenase 1 (soluble) |
| 205349_at | GNA15 | 4.638 | guanine nucleotide binding protein (G protein), alpha 15 (Gq class) |
| 206332_s_at | IFI16 | 4.899 | interferon, gamma-inducible protein 16 |
| 208966_x_at | IFI16 | 4.585 | interferon, gamma-inducible protein 16 |
| 214598_at | CLDN8 | -4.582 | claudin 8 |
| 202017_at | EPHX1 | -4.469 | epoxide hydrolase 1, microsomal (xenobiotic) |
| 211906_s_at | SERPINB4 | 4.911 | serpin peptidase inhibitor, clade B (ovalbumin), member 4 |
| 210413_x_at | SERPINB4 | 4.888 | serpin peptidase inhibitor, clade B (ovalbumin), member 4 |
| 211762_s_at | KPNA2 | 4.76 | karyopherin alpha 2 (RAG cohort 1, importin alpha 1) |
| 201117_s_at | CPE | -4.786 | carboxypeptidase E |
| 206181_at | SLAMF1 | 4.518 | signaling lymphocytic activation molecule family member 1 |
| 204908_s_at | BCL3 | 4.535 | B-cell CLL/lymphoma 3 |
| 200660_at | S100A11 | 4.843 | S100 calcium binding protein A11 |
| 205863_at | S100A12 | 4.627 | S100 calcium binding protein A12 |
| 218142_s_at | CRBN | -4.81 | cereblon |
| 221698_s_at | CLEC7A | 4.84 | C-type lectin domain family 7, member A |
| 208436_s_at | IRF7 | 4.81 | interferon regulatory factor 7 |
| 206561_s_at | AKR1B10 | 4.793 | aldo-keto reductase family 1, member B10 (aldose reductase) |
| 217906_at | KLHDC2 | -4.704 | kelch domain containing 2 |
| 211941_s_at | PEBP1 | -4.772 | phosphatidylethanolamine binding protein 1 |
| 201231_s_at | ENO1 | 4.642 | enolase 1, (alpha) |
| 209185_s_at | IRS2 | -4.557 | insulin receptor substrate 2 |
| 209184_s_at | IRS2 | -4.503 | insulin receptor substrate 2 |
| 205159_at | CSF2RB | 4.829 | colony stimulating factor 2 receptor, beta, low-affinity (granulocyte-macrophage) |
| 212378_at | GART | 4.672 | phosphoribosylglycinamide formyltransferase, phosphoribosylglycinamide synthetase, phosphoribosylaminoimidazole synthetase |

FIG. 1H

| | | | |
|---|---|---|---|
| 210367_s_at | PTGES | 4.815 | prostaglandin E synthase |
| 209720_s_at | SERPINB3 | 4.876 | serpin peptidase inhibitor, clade B (ovalbumin), member 3 |
| 209719_x_at | SERPINB3 | 4.865 | serpin peptidase inhibitor, clade B (ovalbumin), member 3 |
| 213857_s_at | CD47 | 4.888 | CD47 molecule |
| 211075_s_at | CD47 | 4.88 | CD47 molecule |
| 204939_s_at | PLN | -4.537 | phospholamban |
| 214580_x_at | KRT6A | 4.758 | keratin 6A |
| 209125_at | KRT6A | 4.472 | keratin 6A |
| 213603_s_at | RAC2 | 4.67 | ras-related C3 botulinum toxin substrate 2 (rho family, small GTP binding protein Rac2) |
| 206004_at | TGM3 | 4.819 | transglutaminase 3 (E polypeptide, protein-glutamine-gamma-glutamyltransferase) |
| 201697_s_at | DNMT1 | 4.706 | DNA (cytosine-5-)-methyltransferase 1 |
| 33323_r_at | SFN | 4.831 | stratifin |
| 209260_at | SFN | 4.806 | stratifin |
| 200600_at | MSN | 4.566 | moesin |
| 201291_s_at | TOP2A | 4.471 | topoisomerase (DNA) II alpha 170kDa |
| 204580_at | MMP12 | 4.68 | matrix metallopeptidase 12 (macrophage elastase) |
| 205259_at | NR3C2 | -4.545 | nuclear receptor subfamily 3, group C, member 2 |
| 214549_x_at | SPRR1A | 4.695 | small proline-rich protein 1A |
| 208407_s_at | CTNND1 | -4.738 | catenin (cadherin-associated protein), delta 1 |
| 202086_at | MX1 | 4.405 | myxovirus (influenza virus) resistance 1, interferon-inducible protein p78 (mouse) |
| 202054_s_at | ALDH3A2 | -4.854 | aldehyde dehydrogenase 3 family, member A2 |
| 210544_s_at | ALDH3A2 | -4.52 | aldehyde dehydrogenase 3 family, member A2 |
| 204858_s_at | ECGF1 | 4.799 | endothelial cell growth factor 1 (platelet-derived) |
| 202357_s_at | CFB | 4.554 | complement factor B |
| 205774_at | F12 | 4.544 | coagulation factor XII (Hageman factor) |
| 207961_x_at | MYH11 | -4.659 | myosin, heavy chain 11, smooth muscle |
| 201497_x_at | MYH11 | -4.655 | myosin, heavy chain 11, smooth muscle |
| 221748_s_at | TNS1 | -4.716 | tensin 1 |
| 221747_at | TNS1 | -4.697 | tensin 1 |
| 39249_at | AQP3 | 4.91 | aquaporin 3 (Gill blood group) |
| 39248_at | AQP3 | 4.909 | aquaporin 3 (Gill blood group) |
| 203747_at | AQP3 | 4.898 | aquaporin 3 (Gill blood group) |
| 202087_s_at | CTSL1 | 4.543 | cathepsin L1 |

FIG. 1I

| 207277_at | CD209 | 4.724 | CD209 molecule |
|---|---|---|---|
| 203691_at | PI3 | 4.717 | peptidase inhibitor 3, skin-derived (SKALP) |
| 41469_at | PI3 | 4.706 | peptidase inhibitor 3, skin-derived (SKALP) |
| 203256_at | CDH3 | 4.756 | cadherin 3, type 1, P-cadherin (placental) |
| 214710_s_at | CCNB1 | 4.635 | cyclin B1 |
| 202555_s_at | MYLK | -4.653 | myosin, light chain kinase |
| 205916_at | S100A7 | 4.915 | S100 calcium binding protein A7 |
| 219403_s_at | HPSE | 4.843 | heparanase |
| 202345_s_at | FABP5 | 4.513 | fatty acid binding protein 5 (psoriasis-associated) |
| 209124_at | MYD88 | 4.871 | myeloid differentiation primary response gene (88) |
| 202917_s_at | S100A8 | 4.84 | S100 calcium binding protein A8 |
| 205436_s_at | H2AFX | 4.86 | H2A histone family, member X |
| 210987_x_at | TPM1 | -4.725 | tropomyosin 1 (alpha) |
| 208850_s_at | THY1 | 4.786 | Thy-1 cell surface antigen |
| 208851_s_at | THY1 | 4.762 | Thy-1 cell surface antigen |
| 203233_at | IL4R | 4.756 | interleukin 4 receptor |
| 214056_at | MCL1 | 4.676 | myeloid cell leukemia sequence 1 (BCL2-related) |
| 200798_x_at | MCL1 | 4.534 | myeloid cell leukemia sequence 1 (BCL2-related) |
| 201473_at | JUNB | 4.57 | jun B proto-oncogene |
| 202803_s_at | ITGB2 | 4.547 | integrin, beta 2 (complement component 3 receptor 3 and 4 subunit) |
| 209800_at | KRT16 | 4.813 | keratin 16 (focal non-epidermolytic palmoplantar keratoderma) |
| 203416_at | CD53 | 4.691 | CD53 molecule |
| 202805_s_at | ABCC1 | 4.572 | ATP-binding cassette, sub-family C (CFTR/MRP), member 1 |
| 207356_at | DEFB4 | 4.688 | defensin, beta 4 |
| 203535_at | S100A9 | 4.889 | S100 calcium binding protein A9 |
| 213274_s_at | CTSB | 4.685 | cathepsin B |
| 200839_s_at | CTSB | 4.489 | cathepsin B |
| 216841_s_at | SOD2 | 4.663 | superoxide dismutase 2, mitochondrial |
| 204440_at | CD83 | 4.704 | CD83 molecule |
| 206337_at | CCR7 | 4.8 | chemokine (C-C motif) receptor 7 |
| 213348_at | CDKN1C | -4.789 | cyclin-dependent kinase inhibitor 1C (p57, Kip2) |
| 213182_x_at | CDKN1C | -4.658 | cyclin-dependent kinase inhibitor 1C (p57, Kip2) |
| 219534_x_at | CDKN1C | -4.285 | cyclin-dependent kinase inhibitor 1C (p57, Kip2) |
| 202018_s_at | LTF | 4.715 | lactotransferrin |
| 202095_s_at | BIRC5 | 4.425 | baculoviral IAP repeat-containing 5 (survivin) |

FIG. 1J

| | | | |
|---|---|---|---|
| 204363_at | F3 | -4.777 | coagulation factor III (thromboplastin, tissue factor) |
| 217028_at | CXCR4 | 4.748 | chemokine (C-X-C motif) receptor 4 |
| 211919_s_at | CXCR4 | 4.615 | chemokine (C-X-C motif) receptor 4 |
| 204563_at | SELL | 4.567 | selectin L (lymphocyte adhesion molecule 1) |
| 203382_s_at | APOE | -4.482 | apolipoprotein E |
| 205595_at | DSG3 | 4.879 | desmoglein 3 (pemphigus vulgaris antigen) |
| 208820_at | PTK2 | -4.638 | PTK2 protein tyrosine kinase 2 |
| 207233_s_at | MITF | -4.648 | microphthalmia-associated transcription factor |
| 212021_s_at | MKI67 | 4.643 | antigen identified by monoclonal antibody Ki-67 |
| 212022_s_at | MKI67 | 4.394 | antigen identified by monoclonal antibody Ki-67 |
| 206008_at | TGM1 | 4.636 | transglutaminase 1 (K polypeptide epidermal type I, protein-glutamine-gamma-glutamyltransferase) |
| 207238_s_at | PTPRC | 4.521 | protein tyrosine phosphatase, receptor type, C |
| 208992_s_at | STAT3 | 4.517 | signal transducer and activator of transcription 3 (acute-phase response factor) |
| 205051_s_at | KIT | -4.502 | v-kit Hardy-Zuckerman 4 feline sarcoma viral oncogene homolog |
| 209835_x_at | CD44 | 4.64 | CD44 molecule (Indian blood group) |
| 204490_s_at | CD44 | 4.359 | CD44 molecule (Indian blood group) |
| 208712_at | CCND1 | -4.574 | cyclin D1 |
| 213195_at | NOS2A | -4.592 | nitric oxide synthase 2A (inducible, hepatocytes) |
| 202859_x_at | IL8 | 4.716 | interleukin 8 |

SYSTEMS, MODELS AND METHODS FOR IDENTIFYING AND EVALUATING SKIN-ACTIVE AGENTS EFFECTIVE FOR TREATING AN ARRAY OF SKIN DISORDERS

TECHNICAL FIELD

The invention relates to the generation and use of gene expression signatures representative of a plurality of skin conditions.

BACKGROUND

Skin conditions include some of the most common disorders treated in the developing world and represent a significant economic burden, incurring an estimated cost of about $39.3 billion in 2004 in the U.S. alone. ("The Burden of Skin Disease 2004," Prepared for The Society for Investigative Dermatology and The American Academy of Dermatology Association by The Lewin Group, Inc. 2006.) At any moment, one-third of the U.S. population is estimated to actively suffer from at least one skin condition. (Johnson, "Skin conditions and related need for medical care amount persons 1-74 years, United States, 1971-1974." Vital and Health Statistics, Series 11, No. 212, DHEW publication No. (PHS) 79-1660, U.S. Department of Health, Education and Welfare, National Center for Health Statistics 1978: 1-72.) Different skin conditions are associated with widely varied triggers, biological mechanisms, environmental factors, and clinical manifestations, complicating research into skin homeostasis and development of skin care agents with broad applicability.

Acne is a disorder characterized by skin eruptions (including comedones, papules, pustules, and cysts), which commonly occur in areas having a high density of sebaceous glands, including the face, neck, chest, back and shoulders. The skin eruptions occur, for example, when hair follicles are blocked with sebum and dead skin cells. The lesions may be accompanied by inflammation; bacteria, such as *Propionibacterium acnes*, thrive within clogged pores and trigger an inflammatory response. Several factors are believed to contribute to the onset and severity of acne. Although the physical changes within the skin that lead to acne eruptions have been characterized, the underlying causes that dictate which follicles will be affected have proven difficult to identify. Hormonal changes caused by stress, puberty, medications, and pregnancy can increase acne break-outs. Genetic factors also influence the prevalence of acne. Environmental factors, including heat, humidity, and the use of oily or occlusive skin products can also result in acne flare-ups. Diets high in carbohydrates can lead to a worsening of acne (see Smith et al., J Amer Acad of Dermatol, 57 (2): 247-56 (2007)). The development of acne treatments has been hindered because, in part, the root cause of the disorder is not well understood and a myriad of factors may (or may not) play a role in the skin condition. Most current therapies are aimed at treating acne after skin eruptions have occurred to prevent recurring break-outs.

Eczema, also known as dermatitis, is a large class of skin disorders characterized by inflammation leading to red and itchy skin, blisters, and fissures. Eczema is estimated to affect approximately 1 in 10 people world-wide. Types of eczema include neurodermatitis, contact, seborrheic, nummular, and dyshidrotic eczema. The exact cause of eczema is unknown, although the disorder is believed to be influenced by genetic factors, such as a predisposition to allergies or other hypersensitivity. Eczema also has been linked with environmental factors including dry air, cold, and skin irritants. Stress and illness are believed to exacerbate the condition.

Atopic dermatitis, considered a form of eczema, is a chronic skin disorder characterized by scaly and itchy rashes. The disorder can also manifest as skin lesions, discoloration, and eye disorders. Several causes of the disorder have been proposed; however, none have been identified with certainty. Environmental allergens, including food, dust, pollen, and dander, have been linked to the disease. Genetic factors are considered to play a role in the onset of the disease based on family studies (Kluken et al., Allergy, 58(1):5-12 (2003)). Atopic dermatitis has also been linked to changes in genes that lead to defects in the epidermal barrier (Cork et al., J Invest Dermatol., 129(8): 1892-908 (2009)). Environmental factors also influence the development of the disorder; atopic dermatitis has been associated with exposure to radiation from microwaves and cell phones (see, e.g., Kimata et al., Int Arch of Allergy and Immunology, 129 (4):348-350 (2002), and Wang et al., Pediatr Allergy Immunol., 18(5):441-7 (2007)).

Dandruff, alternatively referred to in the literature as ptyriasis simplex, furfuracea or capitis, is a skin disorder characterized by flaking, itching and microinflammation. Dandruff is considered to be a form of seborrheic dermatitis, which may be found in other locations on the body. Generally, dandruff is considered the mildest form of seborrheic dermatitis from a clinical perspective since inflammation is minimal and typically subclinical. In fact, as recently as a decade ago the dandruff condition was thought to be non-inflammatory. Seborrheic dermatitis generally is associated with a higher degree of inflammation.

The pathogenesis of dandruff is complex, and appears to be the result of interactions between scalp skin, cutaneous microflora and the cutaneous immune system. The key clinical features of dandruff include flaking and itch, and the precise underlying events that provoke these symptoms are incompletely understood. Dandruff is considered to have multiple, sometimes overlapping, causes with numerous pathogenic pathways and complex mechanisms. A microbial flora, including, for example, *Malassezia* spp, is implicated in the most common forms of dandruff. Yet, no relationship has been found between severity of symptoms and fungal count. Scaling conditions similar to dandruff may occur following excessive exposure to sunlight, minor chronic irritation of the scalp, over-brushing, over-shampooing, certain cosmetic hair products, and irritation from airborne substances, and psychological stress.

Psoriasis is a chronic disease characterized by an excessive build-up of skin cells. The clinical manifestations of disorder are diverse, and often include plaques of silvery skin, itching, swelling, lesions, and pustules. The flares can occur randomly on different parts of the body. The disease is generally classified into five subtypes, plaque, guttate, inverse, pustular and erythrodermic, each of which are associated with unique characteristics. Severe cases of psoriasis can result in disfigurement and disability. For example, pustular psoriasis can lead to systemic symptoms including fever, chills, weight loss, nausea, headache, joint pain, and fatigue.

The cause of psoriasis and its characteristic overgrowth of skin cells is not well-understood. One hypothesis proposes that the disease is mediated by defects in the immune system, and the disease is believed to have a strong genetic component. Chromosomal loci associated with susceptibility to psoriasis have been identified. Environmental triggers, including injury, smoking, medication, and cold weather, are believed to exacerbate the condition and potentially trigger recurrences. Current treatments seek to minimize the severity of existing flare-ups and minimize recurrence. Many existing treatments, including Enbrel®, Remicade®, and Humira® target the immune system.

Despite the prevalence of skin conditions and research efforts to identify their causes, the underlying mechanisms responsible for many skin conditions remain unclear. The pathogenesis of each, individual condition is multifactorial, and the complex etiologies associated with skin conditions are influenced by a combination of genetic and environmental factors unique to each condition. Indeed, the diverse external and internal stimuli associated with different skin conditions, in combination with an individual's predisposition, and etiological complexity makes a broad spectrum treatment a challenge. There is a persistent need in the art for material and methods for studying the underlying biology of multiple skin conditions, identifying potential skin active agents without reliance on mechanism of action or etiology of a particular condition(s), and determining the influence of agents on skin homeostasis.

The present investigators undertook a transcriptomics investigation of seemingly diverse skin conditions and explored the application of "connectivity mapping" (C-map) to the search for new skin-active agents with broad spectrum efficacy. The general notion that functionality could be accurately determined for previously uncharacterized genes, and that potential targets of drug agents could be identified by mapping connections in a data base of gene expression profiles for drug-treated cells, was spearheaded in 2000 with publication of a seminal paper by T. R. Hughes et al. ["Functional discovery via a compendium of expression profiles" *Cell* 102, 109-126 (2000)], followed shortly thereafter with the launch of The Connectivity Map (-map Project by Justin Lamb and researchers at MIT ("Connectivity Map: Gene Expression Signatures to Connect Small Molecules, Genes, and Disease," *Science*, Vol 313, 2006.) In 2006, Lamb's group began publishing a detailed synopsis of the mechanics of C-map construction and installments of the reference collection of gene expression profiles used to create the first generation C-map and the initiation of an on-going large scale community C-map project, which is available under the "supporting materials" hyperlink at the sciencemag.org website.

Connectivity mapping has achieved in confirmed medical successes with identification of new agents for the treatment of various diseases, including cancer. Nonetheless, certain limiting presumptions challenge application of C-map with respect to diseases of polygenic origin or conditions that are characterized by diverse, and often apparently unrelated, cellular phenotypic manifestations (such as skin conditions). According to Lamb, the challenge to constructing a useful C-map is in the selection of input reference data which permit generation of clinically salient and useful output upon query. For the drug-related C-map of Lamb, strong associations comprise the reference associations, and strong associations are the desired output identified as "hits."

However, agents suitable as pharmaceutical agents and agents suitable as cosmetic agents are categorically distinct. Pharmaceutical agents are selected for specificity and are intended to have measurable effects on structure and function of the body, while cosmetic agents are selected for effect on appearance and may not affect structure and function of the body to a measurable degree. Cosmetic agents also tend to be non-specific with respect to effect on cellular phenotype, and administration to the body is generally limited to application on or close to the body surface.

In constructing C-maps relating to pharmaceutical agents, Lamb stresses that particular difficulty is encountered if reference connections are extremely sensitive and at the same time difficult to detect (weak), and Lamb adopted compromises aimed at minimizing numerous, diffuse associations. Since the regulatory scheme for drug products requires high degrees of specificity between a purported drug agent and disease state, and modulation of disease by impacting a single protein with a minimum of tangential associations is desired in development of pharmaceutical actives, the Lamb C-map is well-suited for screening for potential pharmaceutical agents despite the noted compromises.

The connectivity mapping protocols of Lamb would not be predicted, therefore, to have utility for hypothesis testing/generating in the field of cosmetics and skin care, particularly given the compromises described above. Skin care formulators seek agents or compositions of agents capable of modulating multiple targets and having effects across complex phenotypes and conditions. Further, the phenotypic impact of a skin care agent must be relatively low by definition, so that the agent avoids being subject to the regulatory scheme for pharmaceutical actives. Nonetheless, the impact must be perceptible to the consumer and preferably empirically confirmable by scientific methods. Gene transcription/expression profiles for cosmetic conditions are generally diffuse, comprising many genes with low to moderate fold differentials. Cosmetic agents, therefore, provide more diverse and less acute effects on cellular phenotype and generate the sort of associations expressly taught by Lamb as unsuitable for generating connectivity maps useful for confident hypothesis testing.

Nonetheless, contrary to the teachings of Lamb and the prior art in general, the present investigators surprisingly discovered that useful connectivity maps could be developed to evaluate skin-care actives and cosmetic agents, despite the highly diffuse, systemic and low-level effects these sorts of actives generally engender. Additionally, the value of a connectivity map approach to discover functional connections shared by unhealthy skin phenotypes and study the effects of agents on skin homeostasis is counter-indicated by the progenitors of the drug-based C-map; the relevant phenotypes are very complex, skin condition etiology is not well understood, the genetic perturbations are numerous and weak, and cosmetic agent action is likewise diffuse and, by definition, relatively weak. The successful application of connectivity mapping to target a plurality of biological conditions, each of which is multi-factored and poorly delineated, is a breakthrough in skin care research.

SUMMARY

In order to provide a solution to the problems above, at least one embodiment is directed to a method of evaluating the influence of perturbagens on skin homeostasis. The method comprises causing a computer processor to query a data architecture of stored skin instances with an unhealthy skin gene expression signature. Each skin instance in the data architecture is associated with a perturbagen, and the the query compares the unhealthy skin gene expression signature to each stored skin instance. Also disclosed are systems, data architecture, gene expression signatures and methods of constructing the same suitable for use with the present method. In addition, methods of formulating cosmetic compositions that include perturbagens evaluated according to the present method are disclosed.

BRIEF DESCRIPTION OF THE FIGURES

FIG. 1 is a table listing the up- and down-regulated genes constituting an unhealthy skin gene expression signature representative of a plurality of skin conditions (acne, atopic dermatitis, eczema, dandruff, and psoriasis).

DETAILED DESCRIPTION OF THE INVENTION

Figure 2:
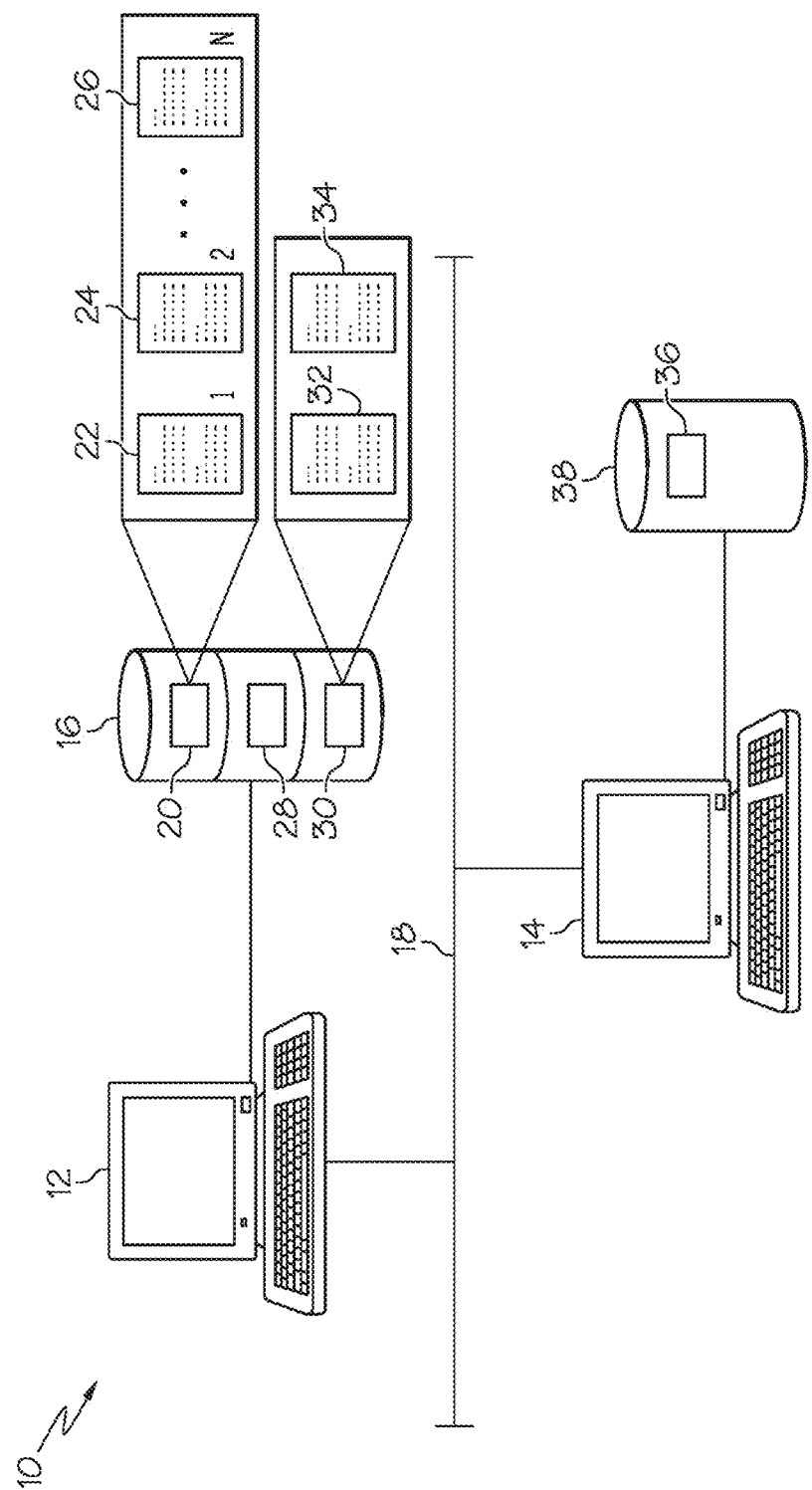
FIG. 2 is a schematic illustration of a computer system suitable for use with the invention.

The invention will now be described with occasional reference to specific embodiments of the invention. This invention may, however, be embodied in different forms and should not be construed as limited to the embodiments set forth herein. Rather, these embodiments are provided so that this disclosure will be thorough and complete, and to fully convey the scope of the invention to those skilled in the art.

Unless otherwise defined, all technical and scientific terms used herein have the same meaning as commonly understood by one of ordinary skill in the art to which this invention pertains. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

As used interchangeably herein, the terms "connectivity map" and "C-map" refer broadly to devices, systems, articles of manufacture, and methodologies for identifying relationships between cellular phenotypes or cosmetic conditions, gene expression, and perturbagens, such as cosmetic actives.

As used herein, the term "cosmetic agent" means any substance, as well as any component thereof, intended to be rubbed, poured, sprinkled, sprayed, introduced into, or otherwise applied to a mammalian body or any part thereof for purposes of cleansing, beautifying, promoting attractiveness, altering the appearance, or combinations thereof. Cosmetic agents include, but are not limited to, substances that are Generally Recognized as Safe (GRAS) by the U.S. Food and Drug Administration, food additives, and materials used in non-cosmetic consumer products including over-the-counter medications. In some embodiments, cosmetic agents may be incorporated in a cosmetic composition comprising a dermatologically acceptable carrier suitable for topical application to skin. A cosmetic agent includes, but is not limited to, (i) chemicals, compounds, small or large molecules, extracts, formulations, or combinations thereof that are known to induce or cause at least one effect (positive or negative) on skin tissue; (ii) chemicals, compounds, small molecules, extracts, formulations, or combinations thereof that are known to induce or cause at least one effect (positive or negative) on skin tissue and are discovered, using the provided methods and systems, to induce or cause at least one previously unknown effect (positive or negative) on the skin tissue; and (iii) chemicals, compounds, small molecules, extracts, formulations, or combinations thereof that are not known have an effect on skin tissue and are discovered, using the provided methods and systems, to induce or cause an effect on skin tissue.

Some examples of cosmetic agents or cosmetically actionable materials can be found in: the PubChem database associated with the National Institutes of Health, USA; the Ingredient Database of the Personal Care Products Council; the 2010 International Cosmetic Ingredient Dictionary and Handbook, 13$^{th}$ Edition, published by The Personal Care Products Council; the EU Cosmetic Ingredients and Substances list; the Japan Cosmetic Ingredients List; the Personal Care Products Council, the SkinDeep database; the FDA Approved Excipients List; the FDA OTC List; the Japan Quasi Drug List; the U.S. FDA Everything Added to Food database; EU Food Additive list; Japan Existing Food Additives, Flavor GRAS list; U.S. FDA Select Committee on GRAS Substances; US Household Products Database; the Global New Products Database (GNPD) Personal Care, Health Care, Food/Drink/Pet and Household database; and from suppliers of cosmetic ingredients and botanicals.

Other non-limiting examples of cosmetic agents include botanicals (which may be derived from one or more of a root, stem bark, leaf, seed or fruit of a plant). Some botanicals may be extracted from a plant biomass (e.g., root, stem, bark, leaf, etc.) using one more solvents. Botanicals may comprise a complex mixture of compounds and lack a distinct active ingredient. Another category of cosmetic agents are vitamin compounds and derivatives and combinations thereof, such as a vitamin B3 compound, a vitamin B5 compound, a vitamin B6 compound, a vitamin B9 compound, a vitamin A compound, a vitamin C compound, a vitamin E compound, and derivatives and combinations thereof (e.g., retinol, retinyl esters, niacinamide, folic acid, panethenol, ascorbic acid, tocopherol, and tocopherol acetate). Other non-limiting examples of cosmetic agents include sugar amines, phytosterols, hexamidine, hydroxy acids, ceramides, amino acids, and polyols.

As used herein, the term "skin-active agent" is a subset of cosmetic agents as defined herein and includes generally any substance, as well as any component thereof, intended to be applied to the skin for the purpose of improving an undesirable skin condition (or symptom thereof), for example, dandruff, seborrheic dermatitis, atopic dermatitis, rash, acne, eczema, psoriasis, or other condition that may be of substantially cosmetic concern. Categorical examples of skin-active agents include, but are not limited to, anti-dandruff actives, steroidal anti-inflammatory agents, non-steroidal anti-inflammatory agents, pediculocides, sensates, enzymes, vitamins, hair growth actives, sunscreens, and combinations thereof. Cosmetic compositions according to the instant invention may contain skin-active agents.

"Dermatologically acceptable carrier" means a carrier that is suitable for topical application to the keratinous tissue. The dermatologically acceptable carrier may be in a wide variety of forms such as, for example, simple solutions (water-based or oil-based), solid forms (e.g., gels or sticks) and emulsions.

The term "gene expression signature" refers to a rationally derived list, or plurality of lists, of genes having an expression pattern that is representative of a skin condition or a biological response to a perturbagen. A gene expression signature generally comprises a combination of genes whose expression, relative to a normal or control state, is increased (up-regulated) and/or decreased (down-regulated), that may serve as proxy for a phenotype of interest. Generally, a gene expression signature for a modified cellular phenotype (e.g., a phenotype observed in response to exposure to a perturbagen or biological challenge or phenotype associated with a skin condition) may be described as a set of genes differentially expressed in the modified cellular phenotype over a control (i.e., wild-type or unaffected cellular phenotype). A gene expression signature can be derived from various sources of data, including but not limited to, in vitro testing, in vivo testing, database information, and combinations thereof. In various embodiments, data associated with a gene expression signature comprises an ordered list of "identifiers" representing differentially expressed genes. Exemplary identifiers include, but are not limited to, gene names, gene symbols, microarray probe set ID values, and combinations thereof. Optionally, a gene expression signature comprises a first list of identifiers representative of a plurality of up-regulated genes of the condition(s) of interest and a second list of identifiers representative of a plurality of down-regulated genes of the condition(s) of interest.

The term "unhealthy skin gene expression signature" refers to a gene expression signature associated with acne, atopic dermatitis, eczema, psoriasis, and dandruff condition, as described further herein.

A "perturbagen" is, for example, a chemical or physical stimulus that evokes a biological response in, for example, skin tissue, leading to a shift in gene expression from normal or wild-type gene expression. Any substance, chemical, compound, small or large molecule, active, natural product (e.g., chemokine), extract, formulation, drug (e.g. Sigma-Aldrich LOPAC (Library of Pharmacologically Active Compounds) collection), and combination thereof can be employed as a perturbagen. "Perturbagen" also includes any other stimulus that generates differential gene expression data. For example, a perturbagen may also be UV radiation, heat, osmotic stress, pH, a microbe, a virus, a recombinant cytokine or growth factor, or small interfering RNA. A perturbagen may be, but is not required to be, a cosmetic agent. In some embodiments, the perturbagen is applied to skin cells and gene expression is measured. The resulting gene expression data is stored, e.g., as an instance in a data architecture.

As used herein, the term "benchmark" agent or perturbagen refers to any chemical, compound, small or large molecule, extract, formulation, or combination thereof that induces or causes a known effect (positive or negative) on, e.g., skin tissue. In various embodiments, the benchmark agent's effect is a robust, desired effect on a cell type or tissue of interest. Non-limiting examples of benchmark agents well-known in the dandruff arts include Zinc pyrithione (ZPT), Selenium sulfide, ketoconazole, Ciclopirox olamine, and coal tar.

As used herein, the term "query" refers to data that is used as an input to a Connectivity Map and against which a plurality of instances are compared. A query may include a gene expression signature associated with skin conditions or an instance. A C-map may be queried with perturbagens, gene expression signatures, skin disorders, thematic signatures, or any data feature or combination of data features or associations that comprise the data architecture.

The term "instance," as used herein, refers to data from a gene expression profiling experiment in which skin cells are dosed with a perturbagen. In some embodiments, the data comprises a list of "identifiers" representing genes, the expression of which is included in the gene expression signature. The identifiers include, for example, gene names, gene symbols, microarray probe set IDs, combinations thereof, or any other identifier. In some embodiments, an instance comprises data from a microarray experiment and comprises a list of probe set IDs of the microarray ordered by the extent of differential expression relative to a control. The data may also comprise metadata, including but not limited to, data relating to one or more of the perturbagen(s), the gene expression profiling test conditions, the skin cells, and the microarray. Numerous instances are publicly available via an on-going, large scale community C-map project, which is available under the "supporting materials" hyperlink at the sciencemag.org website.

The term "dermatologically acceptable," as used herein, means that the compositions or components described are suitable for contact with human skin tissue without undue toxicity, incompatibility, instability, allergic response, and the like.

As used herein, the term "computer readable medium" refers to any electronic storage medium and includes but is not limited to any volatile, nonvolatile, removable, and non-removable media implemented in any method or technology for storage of information such as computer readable instructions, data and data structures, digital files, software programs and applications, or other digital information. Computer readable media includes, but are not limited to, application-specific integrated circuit (ASIC), a compact disk (CD), a digital versatile disk (DVD), a random access memory (RAM), a synchronous RAM (SRAM), a dynamic RAM (DRAM), a synchronous DRAM (SDRAM), double data rate SDRAM (DDR SDRAM), a direct RAM bus RAM (DRRAM), a read only memory (ROM), a programmable read only memory (PROM), an electronically erasable programmable read only memory (EEPROM), a disk, a carrier wave, and a memory stick. Examples of volatile memory include, but are not limited to, random access memory (RAM), synchronous RAM (SRAM), dynamic RAM (DRAM), synchronous DRAM (SDRAM), double data rate SDRAM (DDR SDRAM), and direct RAM bus RAM (DRRAM). Examples of non-volatile memory include, but are not limited to, read only memory (ROM), programmable read only memory (PROM), erasable programmable read only memory (EPROM), and electrically erasable programmable read only memory (EEPROM). A memory can store processes and/or data. Still other computer readable media include any suitable disk media, including but not limited to, magnetic disk drives, floppy disk drives, tape drives, Zip drives, flash memory cards, memory sticks, compact disk ROM (CD-ROM), CD recordable drive (CD-R drive), CD rewriteable drive (CD-RW drive), and digital versatile ROM drive (DVD ROM).

As used herein, the terms "software" and "software application" refer to one or more computer readable and/or executable instructions that cause a computing device or other electronic device to perform functions, actions, and/or behave in a desired manner. The instructions may be embodied in one or more various forms like routines, algorithms, modules, libraries, methods, and/or programs. Software may be implemented in a variety of executable and/or loadable forms and can be located in one computer component and/or distributed between two or more communicating, co-operating, and/or parallel processing computer components and thus can be loaded and/or executed in serial, parallel, and other manners. Software can be stored on one or more computer readable medium and may implement, in whole or part, the methods and functionalities of the invention.

"Skin homeostasis" refers to physiological processes that maintain normal skin growth (e.g., cell renewal and differentiation), structure, and function. Skin barrier function is evaluated using, for example, indicators of barrier integrity and epidermal homeostasis (including biomarkers), transepidermal water loss, moisturization (corneometry), and appearance (optical properties). Disruption of skin homeostasis results in development of skin conditions such as, but not limited to, acne, atopic dermatitis, dyshidrosis, eczema, lichen planus, psoriasis, vitiligo, dandruff, cancer, and the like. Disruption of skin homeostasis also leads to, e.g., fine lines, fine wrinkles and course wrinkles; loss of elasticity or sagging; blotchiness, uneven pigmentation, and discoloration; age spots (areas of discrete pigmentation); enlarged pores; dryness; rough surface texture; translucency or thinness; fragility of the epidermis; impaired tissue repair; and loss of volume.

As used herein, the term "connectivity score" refers to a derived value representing the degree to which an instance correlates to a gene expression signature.

As used herein, the term "data architecture" refers generally to one or more digital data structures comprising an organized collection of data. In some embodiments, the digital data structures can be stored as a digital file (e.g., a spreadsheet file, a text file, a word processing file, a database file, etc.) on a computer readable medium. In some embodiments, the data architecture is provided in the form of a database that may be managed by a database management system (DBMS) that is used to access, organize, and select data (e.g., instances and gene expression signatures) stored in a database.

As used herein, the terms "gene expression profiling" and "gene expression profiling experiment" refer to the measurement of the expression of multiple genes in a biological sample using any technology suitable for detecting and quantifying gene expression. For example, the mRNA expression of thousands of genes may be determined using microarray techniques. Other emerging technologies that may be used include RNA-Seq or whole transcriptome sequencing using NextGen sequencing techniques.

As used herein, the term "microarray" refers broadly to any ordered array of nucleic acids, oligonucleotides, proteins, small molecules, large molecules, and/or combinations thereof on a substrate that enables gene expression profiling of a biological sample. Oligonucleotide arrays typically comprise a plurality of different oligonucleotide probes coupled to a surface of a substrate (e.g., plastic, complex carbohydrate, or acrylic resin) in different known locations. Methods of producing arrays are known to the ordinary skilled practitioner (see, e.g., Bier et al., Adv. Biochem. Eng. Biotechnol., 109:433-53 (2008); Hoheisel, Nat. Rev. Genet., 7:200-10 (2006); Fan et al., Methods Enzymol., 410:57-73 (2006); Raqoussis & Elvidge, Expert Rev. Mol. Diagn., 6:145-52 (2006); Mockler et al., Genomics, 85:1-15 (2005), and references cited therein, the entire teachings of each of which are incorporated by reference herein). The location of probes specific to a particular gene transcript is cataloged, hybridization to the immobilized probe is detected, and the polynucleotide is identified by the location of the hybridization on the array. Non-limiting examples of microarrays are available from Affymetrix, Inc.; Agilent Technologies, Inc.; Ilumina, Inc.; GE Healthcare, Inc.; Applied Biosystems, Inc.; and Beckman Coulter, Inc.

Unless otherwise indicated, all numbers expressing quantities of ingredients, properties such as molecular weight, reaction conditions, and so forth as used in the specification and claims are to be understood as being modified in all instances by the term "about." Additionally, the disclosure of any ranges in the specification and claims are to be understood as including the range itself and also anything subsumed therein, as well as endpoints. All numeric ranges are inclusive of narrower ranges; delineated upper and lower range limits are interchangeable to create further ranges not explicitly delineated. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

Devices, systems and methods are provided for constructing a gene expression signature representative for a plurality of biological conditions. In various aspects, the gene expression signature is an unhealthy skin expression signature representative of a plurality of skin conditions, regardless of etiology or clinical presentation. An unhealthy skin gene expression signature as described herein is a valuable tool for, e.g., identifying skin-active agents effective against multiple skin conditions, which is otherwise challenging given the widely variable clinical manifestations and elusive biology underlying different skin conditions. An unhealthy skin gene expression signature is similarly a valuable tool to identify biomarkers of fundamental importance in the establishment and maintenance of homeostasis in the skin or other epithelia, as the signature comprises a set of genes whose expression is perturbed regardless of precise trigger(s) or clinical presentation of the various skin conditions.

Devices, systems and methods also are provided for evaluating the influence of perturbagens on skin homeostasis, thereby potentially identifying connections (i.e., relationships) between perturbagens and skin health. The method comprises causing a computer to query a data architecture of stored skin instances, each skin instance being associated with a perturbagen, with an unhealthy skin gene expression signature. The querying comprises comparing the unhealthy skin gene expression signature to each stored skin instance. The in silico method facilitates identification of perturbagens that induce a statistically significant change in expression of a statistically significant number of genes associated with a plurality of skin conditions of interest (e.g., acne, atopic dermatitis, eczema, dandruff, and psoriasis), leading to the identification of new cosmetic agents for treating skin conditions or new uses of known cosmetic agents. For example, in one aspect of the invention, a method for formulating a skin care composition is provided. The method comprises accessing with a computer a plurality of instances stored on at least one computer readable medium, accessing with a computer at least one unhealthy skin gene expression signature stored on the at least one computer readable medium, comparing with a computer the unhealthy skin gene expression signature to the plurality of the instances, assigning with a computer a connectivity score to each of the plurality of instances, and formulating a skin care composition comprising a dermatologically acceptable carrier and at least one perturbagen associated with an instance having a negative correlation (i.e., a negative connectivity score).

Features of the invention are further described below. Section headings are for convenience of reading and not intended to be limiting per se. The entire document is intended to be related as a unified disclosure, and it should be understood that all combinations of features described herein are contemplated, even if the combination of features are not found together in the same sentence, or paragraph, or section of this document.

Methods for Constructing a Gene Expression Signature

The invention is predicated, at least in part, on the development of a method for identifying relationships between two or more data sets, each having multiple measured features. In one aspect, the invention provides a method for identifying a gene expression signature that is representative of a plurality of biological conditions. In the context of skin health, the precise causes of many skin conditions, including acne, atopic dermatitis, eczema, dandruff, and psoriasis, are not well understood. Additionally, the pathogenesis of skin conditions typically involves complex processes involving numerous known and unknown extrinsic and intrinsic factors. Each skin condition also is accompanied by different clinical features. Indeed, symptoms can vary widely between different individuals suffering from the same condition. The method described herein remarkably yields a gene expression signature that is representative of diverse biological (e.g., skin) conditions.

The invention provides a method for constructing a gene expression signature. The method comprises (a) obtaining gene expression measurements for a plurality of biological conditions; (b) identifying genes differentially expressed in the biological conditions by comparing the gene expression measurements of (a) with gene expression measurements for a control sample; (c) causing a computer to calculate a gene expression consistency value. The consistency value is representative of the significance of the difference in expression among the plurality of conditions. The method further comprises (d) creating an ordered list comprising identifiers representing consistently differentially expressed genes (i.e., genes differentially expressed in the tested biological conditions compared to the control sample), wherein the identifiers are ordered according to the gene expression consistency value computed in (c); and (e) storing the ordered list as a gene expression signature on at least one computer readable medium. The method optionally comprises using a programmable computer to perform one or more of steps (b), (c), (d), or (e).

To calculate the gene expression consistency value, log-odds ratios are computed for the differentially expressed genes, and the log-odds ratios are transformed using a sigmoid function. The method further comprises performing a one-tailed t-test against zero, and computing log-odds ratios from the one-tailed t-test. The resulting gene expression consistency value is used to generate an ordered list of identifiers representing genes that are differentially expressed in the biological conditions of interest. The ordered list of identifiers is optionally associated with a numerical ranking for the identifier corresponding to its rank in the ordered list.

A "biological condition" is any phenotype of interest, including an abnormal phenotype associated with disease, biological disorder, malnutrition, age, and infection. In various aspects of the invention, the biological conditions are skin conditions; however, the method is applicable to other non-skin-related conditions. A "control sample" is a matched sample (e.g., the same cell type used to generate the gene expression measurements for the plurality of biological conditions) that is not afflicted with the biological condition. For example, the gene expression measurements from a control sample is generated from a biological sample taken earlier in time, prior to suffering from the biological condition; a control subject or population whose gene expression measurements are known; or an index value or baseline value. A control gene expression profile can also be derived from prediction algorithms or computed indices from population studies. In various embodiments, the control sample is matched for race, gender, age, geographic location, and/or ethnic origin with respect to origin of the gene expression measurements of the plurality of biological disorders.

Measuring Gene Expression

In various aspects, the invention comprises obtaining one or more gene expression measurements, such as gene expression measurements in a plurality of biological samples representing a plurality of biological conditions (i.e., at least two of the biological samples exhibit different biological conditions). Gene expression measurements comprise quantitative or qualitative expression data for a number of genes. The gene expression profile is examined or measured in any suitable biological sample, e.g., a human biological sample. In the context of skin disorders, gene expression measurements may be obtained from full thickness skin biopsies from skin afflicted with the skin condition(s). For generation of dandruff gene expression profiles, for example, biopsies are taken from dandruff-affected scalp skin. The gene expression measurements are compared to non-dandruff affected scalp skin sampled from an anatomically comparable site in an unaffected subject (i.e., a control sample). Alternatively or in addition, gene expression measurements may be obtained from keratinocyte cells challenged in vitro to mimic a biological disorder of interest.

Gene expression is detected and/or measured in a variety of ways. Exemplary biomolecules representative of gene expression (i.e., "biomarkers") include protein, nucleic acid (e.g., mRNA, microRNA, or cDNA), protein fragments or metabolites, and/or products of enzymatic activity encoded by the protein encoded by a gene transcript, and detection and/or measurement of any of the biomarkers described herein is suitable in the context of the invention. In one embodiment, the method comprises measuring mRNA encoded by one or more of the genes. If desired, the method comprises reverse transcribing mRNA encoded by one or more of the genes and measuring the corresponding cDNA. Any quantitative nucleic acid assay may be used. For example, many quantitative hybridization, Northern blot, and polymerase chain reaction procedures exist for quantitatively measuring the amount of an mRNA transcript or cDNA in a biological sample. See, e.g., Current Protocols in Molecular Biology, Ausubel et al., eds., John Wiley & Sons (2007), including all supplements. Optionally, the mRNA or cDNA is amplified by polymerase chain reaction (PCR) prior to hybridization. The mRNA or cDNA sample is then examined by, e.g., hybridization with oligonucleotides specific for mRNAs or cDNAs encoded by one or more of the genes of the panel, optionally immobilized on a substrate (e.g., an array or microarray). Selection of one or more suitable probes specific for an mRNA or cDNA, and selection of hybridization or PCR conditions, are within the ordinary skill of scientists who work with nucleic acids. Binding of the biomarker nucleic acid to oligonucleotide probes specific for the biomarker(s) allows identification and quantification of the biomarker.

The invention also contemplates measuring protein encoded by one or more of the genes. Any technique for quantifying a protein may be used for quantifying proteins in the context of the invention. For example, quantitative mass spectrometry is suitable for measuring protein in a sample, including measuring small amounts of protein in a small sample. Numerous antibody-based methods exist for quantifying proteins in samples, including Western blot techniques and ELISA assays. For biomarkers having biological activity (e.g., enzymatic activity), measurement of the activity of one or more biomarkers may be used as a surrogate for measuring gene expression. In a typical enzymatic activity assay, for example, a biological sample or fraction thereof is contacted with a substrate for the enzyme under conditions suitable for enzymatic activity, and product of the enzymatic reaction is measured over time.

In some variations, a protein is identified and/or quantified with an immunoassay, using one or more antibodies that preferentially bind, and preferably bind with high specificity, to a protein of interest. Exemplary immunoassays include immunofluorescent immunoassays, immunoprecipitations, radioimmunoasays, ELISA, and Western blotting. The epitope(s) used for recognizing and quantifying a protein may be a linear peptide epitope, a conformational epitope, an epitope that includes one or more side-chain modifications (e.g., glycosylation), and so on. See generally E. Maggio, Enzyme-Immunoassay, (1980) (CRC Press, Inc., Boca Raton, Fla.). See also U.S. Pat. Nos. 4,727,022; 4,659,678; 4,376,110; 4,275,149; 4,233,402, and 4,230,767.

An exemplary method of measuring gene expression and comparing the gene expression measurements to reference gene expression measurements (taken from a control sample) is described below with reference to FIG. 5. mRNA is extracted from a biological sample and transcribed to cDNA, which is marked with different fluorescent dyes (e.g., red and green) if a two color microarray analysis is performed. Alternatively, the samples are prepped for a one color microarray analysis, and further a plurality of replicates is processed if desired. Optionally, the procedure also is carried out on a reference (control) sample. The cDNA samples are co-hybridized to the microarray 80 comprising a plurality (e.g., tens, hundreds, or thousands) of probes 82. In one aspect, each probe on the microarray has a unique probe set identifier. The microarray is scanned by a scanner 84, which excites the dyes and measures the amount of fluorescence. A computing device 86 analyzes the raw images to determine the amount of cDNA, which is representative of the expression levels of a gene. The scanner 84 may incorporate the functionality of the computing device 86. Gene expression data collected by the system include: i) up-regulation of gene expression (e.g., greater binding of the test material (e.g., cDNA 74, 76) to probes compared to reference material (e.g., cDNA 78)), ii) down-regulation of gene expression (e.g., reduced binding of the test material (e.g., cDNA 74, 76) to probes than the test material (e.g., cDNA 78)), iii) non-fluctuating gene expression (e.g., similar binding of the test material (e.g., cDNA 74, 76) to the probes compared to the reference material (e.g., cDNA 78)), and iv) no detectable signal or noise. The up- and down-regulated genes are referred to as "differentially expressed."

Microarrays and microarray analysis techniques are well known in the art, and it is contemplated that other microarray techniques may be used with the methods, devices, and systems of the invention. For example, any suitable commercial or non-commercial microarray technology and associated techniques may used, such as, but not limited to Affymetrix GeneChip™ technology and Illumina Bead-Chip™ technology. One of skill in the art will appreciate that the invention is not limited to the methodology described above, and that other methods and techniques are also contemplated to be within its scope of the invention.

Unhealthy Skin Gene Expression Signature

In one embodiment, the gene expression signature is an unhealthy skin gene expression signature, and the plurality of biological conditions is a plurality of skin conditions (e.g., any combination of acne, atopic dermatitis, eczema, dandruff, and psoriasis). As used herein, an "unhealthy skin gene expression signature" comprises one or more gene expression signature lists of identifiers representing a plurality of genes with enhanced (up-regulated) and/or diminished (down-regulated) expression in acne, atopic dermatitis, eczema, dandruff, and psoriasis. The pattern of expression is representative of the skin conditions. As described in greater detail in the Examples, a number of gene transcripts were identified that are present in increased or decreased levels in individuals suffering from acne, atopic dermatitis, eczema, dandruff, and psoriasis. A list of the gene transcripts is provided in FIG. 1. A subset of the gene transcripts in FIG. 1 is set forth in Tables A and B below, which provides the acronym and description of the protein corresponding to the identified gene transcript, the gene expression consistency value, as well as the Affymetrix probe identifier from AFFYMETRIX_3PRIME_IVT_ID (Affymetrix GeneChip® Human Genome U133 (HG-U133) Plus 2.0 Array (by Affymetrix, Inc. Santa Clara, Calif. 95051 USA) that binds the gene transcript.

TABLE A

TOP 70 UP-REGULATED GENES

| Probe Id | Gene Symbol | Consistency Value | Description |
|---|---|---|---|
| 206276_at | LY6D | 4.91528 | lymphocyte antigen 6 complex, locus D |
| 205916_at | S100A7 | 4.915139 | S100 calcium binding protein A7 |
| 211906_s_at | SERPINB4 | 4.910778 | serpin peptidase inhibitor, clade B (ovalbumin), member 4 |
| 39249_at | AQP3 | 4.910101 | aquaporin 3 (Gill blood group) |
| 39248_at | AQP3 | 4.909024 | aquaporin 3 (Gill blood group) |
| 219630_at | PDZK1IP1 | 4.903049 | PDZK1 interacting protein 1 |
| 208539_x_at | SPRR2D | 4.902966 | small proline-rich protein 2D |

TABLE A-continued

TOP 70 UP-REGULATED GENES

| Probe Id | Gene Symbol | Consistency Value | Description |
|---|---|---|---|
| 206332_s_at | IFI16 | 4.898821 | interferon, gamma-inducible protein 16 |
| 203747_at | AQP3 | 4.898464 | aquaporin 3 (Gill blood group) |
| 210138_at | RGS20 | 4.896669 | regulator of G-protein signaling 20 |
| 201739_at | SGK | 4.895065 | serum/glucocorticoid regulated kinase |
| 201644_at | TSTA3 | 4.891853 | tissue specific transplantation antigen P35B |
| 36936_at | TSTA3 | 4.891846 | tissue specific transplantation antigen P35B |
| 203535_at | S100A9 | 4.889123 | S100 calcium binding protein A9 |
| 210413_x_at | SERPINB4 | 4.888317 | serpin peptidase inhibitor, clade B (ovalbumin), member 4 |
| 213857_s_at | CD47 | 4.888204 | CD47 molecule |
| 206628_at | SLC5A1 | 4.888157 | solute carrier family 5 (sodium/glucose cotransporter), member 1 |
| 220658_s_at | ARNTL2 | 4.885055 | aryl hydrocarbon receptor nuclear translocator-like 2 |
| 211075_s_at | CD47 | 4.879618 | CD47 molecule |
| 205595_at | DSG3 | 4.879389 | desmoglein 3 (pemphigus vulgaris antigen) |
| 209720_s_at | SERPINB3 | 4.876346 | serpin peptidase inhibitor, clade B (ovalbumin), member 3 |
| 209124_at | MYD88 | 4.871433 | myeloid differentiation primary response gene (88) |
| 208865_at | CSNK1A1 | 4.870978 | casein kinase 1, alpha 1 |
| 209719_x_at | SERPINB3 | 4.865416 | serpin peptidase inhibitor, clade B (ovalbumin), member 3 |
| 205436_s_at | H2AFX | 4.860126 | H2A histone family, member X |
| 207168_s_at | H2AFY | 4.858992 | H2A histone family, member Y |
| 200660_at | S100A11 | 4.842892 | S100 calcium binding protein A11 |
| 219403_s_at | HPSE | 4.842814 | heparanase |
| 221698_s_at | CLEC7A | 4.840473 | C-type lectin domain family 7, member A |
| 202917_s_at | S100A8 | 4.840094 | S100 calcium binding protein A8 |
| 220966_x_at | ARPC5L | 4.834322 | actin related protein 2/3 complex, subunit 5-like |
| 217755_at | HN1 | 4.833366 | hematological and neurological expressed 1 |
| 204300_at | PET112L | 4.832073 | PET112-like (yeast) |
| 33323_r_at | SFN | 4.831136 | stratifin |
| 205159_at | CSF2RB | 4.828728 | colony stimulating factor 2 receptor, beta, low-affinity (granulocyte-macrophage) |
| 205847_at | PRSS22 | 4.824224 | protease, serine, 22 |
| 206004_at | TGM3 | 4.818552 | transglutaminase 3 (E polypeptide, protein-glutamine-gamma-grutamyltransferase) |
| 220664_at | SPRR2C | 4.817313 | small proline-rich protein 2C |
| 200734_s_at | ARF3 | 4.815111 | ADP-ribosylation factor 3 |
| 210367_s_at | PTGES | 4.814893 | prostaglandin E synthase |
| 209800_at | KRT16 | 4.812639 | keratin 16 (focal non-epidermolytic palmoplantar keratoderma) |
| 204715_at | PANX1 | 4.812402 | pannexin 1 |
| 208436_s_at | IRF7 | 4.810156 | interferon regulatory factor 7 |
| 217834_s_at | SYNCRIP | 4.807022 | synaptotagmin binding, cytoplasmic RNA interacting protein |
| 209260_at | SFN | 4.805903 | stratifin |
| 222062_at | IL27RA | 4.804355 | interleukin 27 receptor, alpha |
| 206337_at | CCR7 | 4.799916 | chemokine (C-C motif) receptor 7 |
| 204858_s_at | ECGF1 | 4.799228 | endothelial cell growth factor 1 (platelet-derived) |
| 206561_s_at | AKR1B10 | 4.792698 | aldo-keto reductase family 1, member B10 (aldose reductase) |
| 201594_s_at | PPP4R1 | 4.792561 | protein phosphatase 4, regulatory subunit 1 |
| 214226_at | POL3S | 4.786843 | polyserase 3 |
| 208850_s_at | THY1 | 4.785561 | Thy-1 cell surface antigen |
| 209191_at | TUBB6 | 4.785294 | tubulin, beta 6 |
| 208696_at | CCT5 | 4.78084 | chaperonin containing TCP1, subunit 5 (epsilon) |
| 201422_at | IFI30 | 4.773338 | interferon, gamma-inducible protein 30 |
| 219956_at | GALNT6 | 4.773242 | UDP-N-acetyl-alpha-D-galactosamine:polypeptide N-acetylgalactosaminyltransferase 6 (GalNAc-T6) |
| 213923_at | RAP2B | 4.770723 | RAP2B, member of RAS oncogene family |
| 219099_at | C12orf5 | 4.769984 | chromosome 12 open reading frame 5 |
| 208540_x_at | S100A11P | 4.76545 | S100 calcium binding protein A11 pseudogene |
| 218960_at | TMPRSS4 | 4.764691 | transmembrane protease, serine 4 |
| 208851_s_at | THY1 | 4.762465 | Thy-1 cell surface antigen |
| 209825_s_at | UCK2 | 4.761794 | uridine-cytidine kinase 2 |
| 211762_s_at | KPNA2 | 4.760486 | karyopherin alpha 2 (RAG cohort 1, importin alpha 1) |
| 214580_x_at | KRT6A | 4.758303 | keratin 6A |
| 201890_at | RRM2 | 4.75819 | ribonucleotide reductase M2 polypeptide |

TABLE A-continued

TOP 70 UP-REGULATED GENES

| Probe Id | Gene Symbol | Consistency Value | Description |
|---|---|---|---|
| 220322_at | IL1F9 | 4.757994 | interleukin 1 family, member 9 |
| 203233_at | IL4R | 4.756367 | interleukin 4 receptor |
| 203256_at | CDH3 | 4.756347 | cadherin 3, type 1, P-cadherin (placental) |
| 218335_x_at | TNIP2 | 4.748637 | TNFAIP3 interacting protein 2 |
| 217028_at | CXCR4 | 4.74826 | chemokine (C-X-C motif) receptor 4 |

TABLE B

TOP 70 DOWN-REGULATED GENES

| Probe Id | Gene Symbol | Consistency Value | Description |
|---|---|---|---|
| 205325_at | PHYHIP | −4.88711 | phytanoyl-CoA 2-hydroxylase interacting protein |
| 221249_s_at | FAM117A | −4.88637 | family with sequence similarity 117, member A |
| 204872_at | TLE4 | −4.86431 | transducin-like enhancer of split 4 (E(sp1) homolog, *Drosophila*) |
| 202976_s_at | RHOBTB3 | −4.85966 | Rho-related BTB domain containing 3 |
| 218471_s_at | BBS1 | −4.85905 | Bardet-Biedl syndrome 1 |
| 203697_at | FRZB | −4.85676 | frizzled-related protein |
| 209292_at | ID4 | −4.85639 | inhibitor of DNA binding 4, dominant negative helix-loop-helix protein |
| 204589_at | NUAK1 | −4.8556 | NUAK family, SNF1-like kinase, 1 |
| 202054_s_at | ALDH3A2 | −4.85364 | aldehyde dehydrogenase 3 family, member A2 |
| 206149_at | CHP2 | −4.85176 | calcineurin B homologous protein 2 |
| 218087_s_at | SORBS1 | −4.84279 | sorbin and SH3 domain containing 1 |
| 21778 l_s_at | ZFP106 | −4.83695 | zinc finger protein 106 homolog (mouse) |
| 221527_s_at | PARD3 | −4.83187 | par-3 partitioning defective 3 homolog (*C. elegans*) |
| 218820_at | C14orf132 | −4.83174 | chromosome 14 open reading frame 132 |
| 218528_s_at | RNF38 | −4.82082 | ring finger protein 38 |
| 218142_s_at | CRBN | −4.80965 | cereblon |
| 205807_s_at | TUFT1 | −4.7983 | tuftelin 1 |
| 203698_s_at | FRZB | −4.79519 | frizzled-related protein |
| 221834_at | LONP2 | −4.79387 | lon peptidase 2, peroxisomal |
| 213348_at | CDKN1C | −4.78917 | cyclin-dependent kinase inhibitor 1C (p57, Kip2) |
| 201117_s_at | CPE | −4.78562 | carboxypeptidase E |
| 204363_at | F3 | −4.77707 | coagulation factor III (thromboplastin, tissue factor) |
| 204032_at | BCAR3 | −4.77577 | breast cancer anti-estrogen resistance 3 |
| 213227_at | PGRMC2 | −4.77522 | progesterone receptor membrane component 2 |
| 211941_s_at | PEBP1 | −4.77192 | phosphatidylethanolamine binding protein 1 |
| 222362_at | 222362_at | −4.77075 | 222362_at |
| 221476_s_at | RPL15 | −4.76783 | ribosomal protein L15 |
| 209291_at | ID4 | −4.74821 | inhibitor of DNA binding 4, dominant negative helix-loop-helix protein |
| 212071_s_at | SPTBN1 | −4.74168 | spectrin, beta, non-erythrocytic 1 |
| 208407_s_at | CTNND1 | −4.73848 | catenin (cadherin-associated protein), delta 1 |
| 208655_at | CCNI | −4.73802 | cyclin I |
| 219132_at | PELI2 | −4.73515 | pellino homolog 2 (*Drosophila*) |
| 212321_at | SGPL1 | −4.72991 | sphingosine-1-phosphate lyase 1 |
| 210987_x_at | TPM1 | −4.72527 | tropomyosin 1 (alpha) |
| 203766_s_at | LMOD1 | −4.72398 | leiomodin 1 (smooth muscle) |
| 203296_s_at | ATP1A2 | −4.72261 | ATPase, Na+/K+ transporting, alpha 2 (+) polypeptide |
| 212510_at | GPD1L | −4.72061 | glycerol-3-phosphate dehydrogenase 1-like |
| 221748_s_at | TNS1 | −4.71615 | tensin 1 |
| 215945_s_at | TRIM2 | −4.7111 | tripartite motif-containing 2 |
| 217906_at | KLHDC2 | −4.70413 | kelch domain containing 2 |
| 203081_at | CTNNBIP1 | −4.70276 | catenin, beta interacting protein 1 |
| 215235_at | SPTAN1 | −4.6997 | spectrin, alpha, non-erythrocytic 1 (alpha-fodrin) |
| 218625_at | NRN1 | −4.69941 | neuritin 1 |
| 221747_at | TNS1 | −4.69743 | tensin 1 |
| 209108_at | TSPAN6 | −4.68026 | tetraspanin 6 |
| 201701_s_at | PGRMC2 | −4.6688 | progesterone receptor membrane component 2 |
| 205412_at | ACAT1 | −4.66772 | acetyl-Coenzyme A acetyltransferase 1 (acetoacetyl Coenzyme A thiolase) |
| 203824_at | TSPAN8 | −4.66262 | tetraspanin 8 |
| 207961_x_at | MYH11 | −4.65866 | myosin, heavy chain 11, smooth muscle |
| 213182_x_at | CDKN1C | −4.65816 | cyclin-dependent kinase inhibitor 1C (p57, Kip2) |
| 201989_s_at | CREBL2 | −4.65632 | cAMP responsive element binding protein-like 2 |
| 212372_at | MYH10 | −4.6558 | myosin, heavy chain 10, non-muscle |

TABLE B-continued

TOP 70 DOWN-REGULATED GENES

| Probe Id | Gene Symbol | Consistency Value | Description |
| --- | --- | --- | --- |
| 201497_x_at | MYH11 | −4.65524 | myosin, heavy chain 11, smooth muscle |
| 219440_at | RAI2 | −4.65521 | retinoic acid induced 2 |
| 202555_s_at | MYLK | −4.65344 | myosin, light chain kinase |
| 202747_s_at | ITM2A | −4.64968 | integral membrane protein 2A |
| 207233_s_at | MITF | −4.64829 | microphthalmia-associated transcription factor |
| 217897_at | FXYD6 | −4.6416 | FXYD domain containing ion transport regulator 6 |
| 202724_s_at | FOXO1 | −4.64107 | forkhead box O1 |
| 219304_s_at | PDGFD | −4.64071 | platelet derived growth factor D |
| 204712_at | WIF1 | −4.63919 | WNT inhibitory factor 1 |
| 208820_at | PTK2 | −4.63758 | PTK2 protein tyrosine kinase 2 |
| 209733_at | MID2 | −4.62576 | midline 2 |
| 206015_s_at | FOXJ3 | −4.62383 | forkhead box J3 |
| 213900_at | C9orf61 | −4.62262 | chromosome 9 open reading frame 61 |
| 203498_at | RCAN2 | −4.6204 | regulator of calcineurin 2 |
| 209071_s_at | RGS5 | −4.6203 | regulator of G-protein signaling 5 |
| 213050_at | COBL | −4.61803 | cordon-bleu homolog (mouse) |
| 221958_s_at | GPR177 | −4.61747 | G protein-coupled receptor 177 |
| 218418_s_at | ANKRD25 | −4.6141 | ankyrin repeat domain 25 |

While a gene expression signature may represent all significantly regulated genes associated with biological (e.g., skin) conditions of interest; typically it represents a subset of such genes. In the "unhealthy skin gene expression signature" of the invention, the plurality of genes includes at least one gene (e.g., at least two, at least three, at least four, at least five, at least six, at least seven, at least eight, at least nine, or at least ten genes) selected from the group consisting of TSTA3, ARPC5L, SYNCRIP, PPP4R1, POL3S, TUBB6, CCT5, GALNT6, C12orf5, S100A11P, TNIP2, DIMT1L, OTUB1, MPZL2, DDX39, EIF6, PLSCR3, LAPTM5, MPZL2, SAMSN1, SLC43A3, ZWINT, EHBP1L1, TRIM14, HNRNPA2B1, TNIP2, EBNA1BP2, SECTM1, FAIM3, N4BP1, N4BP1, SNRPD3, LAPTM5, LOC391020, TRABD, C20orf11, 216952_s_at, LMOD1, C14orf132, GPD1L, TRIM2, RNF38, LONP2, 222362_at, PHYHIP, FAM117A, RHOBTB3, NUAK1, CHP2, CREBL2, RAI2, FXYD6, MID2, CCNI, PELI2, FOXJ3, ANKRD25, IAA0265, FLJ10357, OSBPL1A, DDX42, C1orf115, C21orf25, TTC3, RPS14, 212498_at, PFAAP5, TSPYL5212970_at, C6orf48, IHPK2, and RP4-691N24.1. For example, the plurality of genes comprises at least one up-regulated gene selected from the group consisting of TSTA3, ARPC5L, SYNCRIP, PPP4R1, POL3S, TUBB6, CCT5, GALNT6, C12orf5, S100A11P, TNIP2, DIMT1L, OTUB1, MPZL2, DDX39, EIF6, PLSCR3, LAPTM5, MPZL2, SAMSN1, SLC43A3, ZWINT, EHBP1L1, TRIM14, HNRNPA2B1, TNIP2, EBNA1BP2, SECTM1, FAIM3, N4BP1, N4BP1, SNRPD3, LAPTM5, LOC391020, TRABD, C20orf11, and 216952_s_at, such as at least one up-regulated gene selected from the group consisting of TSTA3, ARPC5L, SYNCRIP, PPP4R1, POL3S, TUBB6, CCT5, GALNT6, C12orf5, S100A11P, and TN1P2. Alternatively or in addition, the plurality of genes included in the unhealthy skin gene expression signature comprises at least one down-regulated gene selected from the group consisting of LMOD1, C14orf132, GPD1L, TRIM2, RNF38, LONP2, 222362_at, PHYHIP, FAM117A, RHOBTB3, NUAK1, CHP2, CREBL2, RAI2, FXYD6, MID2, CCNI, PELI2, FOXJ3, ANKRD25, IAA0265, FLJ10357, OSBPL1A, DDX42, C1orf115, C21orf25, TTC3, RPS14, 212498_at, PFAAP5, TSPYL5212970_at, C6orf48, IHPK2, and RP4-691N24.1, such as at least one down-regulated gene selected from the group consisting of PHYHIP, FAM117A, PHOBTB3, CHP2, C14orf132, LONP2, 222362-at, CCNI, PELI2, LMOD1, GPD1L, TRIM2, CREBL2, RAI2, FXYD6, MID2, FOXJ3, and ANKRD25.

The unhealthy skin gene expression signature optionally comprises between about 80% and about 100% of the up-regulated genes set forth in Table A and/or between about 80% and about 100% of the down-regulated genes set forth in Table B, which represent the 70 most up- and down-regulated genes common in acne, psoriasis, dandruff, atopic dermatitis, and eczema. The unhealthy skin gene expression signature comprises, in various embodiments, between about 80% and about 100% of the genes set forth in FIG. 1. In some aspects, the unhealthy skin gene expression signature is limited to the genes set forth in Tables A or B or FIG. 1, although expression of additional genes may be included as part of the gene expression signature in other embodiments of the invention.

In various aspects, the gene expression signature references at least two, at least four, at least five, at least 10, at least 20, at least 25, at least 30, or at least 50 genes (e.g., 75 or more genes). Alternatively or in addition, the gene expression signature references no more than 10,000, no more than 7,500, no more than 5,000, no more than 1,000, no more than 800, no more than 750, no more than 700, no more than 500, no more than 450, no more than 400, no more than 350, no more than 300, no more than 250, no more than 200, no more than 150, no more than 100, no more than 70, no more than 50, or no more than 20 genes. For example, the gene expression signature optionally comprises identifiers corresponding to between about 5 and about 800 genes (e.g., between about 5 and about 400 genes, between about 10 and about 400 genes, between about 10 and about 200 genes, or between about 10 and about 140 genes). Exemplary unhealthy skin gene expression signatures comprise between about 100 and about 400 genes of approximately equal numbers of up-regulated and/or down-regulated genes. For example, a suitable gene expression signature optionally comprises from about 100-150 genes, about 250-300 genes, about 300-350 genes, or about 350-400 genes.

The number of genes will vary from biological condition to biological condition. When the biology is weaker, such as is the case typically with cosmetic condition phenotypes, fewer genes than those which may meet the statistical requisite for inclusion in the prior art, may be used to avoid adding genes that contribute to "noise." For example, where gene expression profiling analysis of a skin condition yields from between about 2,000 and 4,000 genes having a statistical p-value of less than 0.05 and approximately 1000 genes having a p-value of less than 0.001, a very strong biological response is indicated. A moderately strong biological response may yield approximately 800-2000 genes that have a statistical p-value of less than 0.05 combined with approximately 400-600 genes that have a p-value of less than 0.001. In these cases, a gene expression signature optionally comprises between about 100 and about 600 genes. Weaker biology is optionally represented by a gene expression signature comprising fewer genes, such as between about 20 and 100 genes. The invention further provides an immobilized array of oligonucleotides which hybridize to transcripts of between about 10 and about 400 genes, wherein the genes are selected from FIG. 1 (e.g., the genes are selected from Table A and Table B).

While the unhealthy skin gene expression signature was generated using gene expression profiles of acne, atopic dermatitis, psoriasis, eczema, and dandruff, the signature remarkably also displays very strong linkages in connectivity mapping (described further herein) with melanoma, nevus, inflammatory bowel disease, inflamed colonic mucosa, atypical ductal hyperplasia (breast), pre-cancerous adenoma, gingival epithelium, and nickel-exposed skin (a known type IV allergen). Thus, the invention further contemplates use of the unhealthy skin gene expression signature in methods of evaluating the influence of perturbagen(s) on these conditions.

In some embodiments, a gene expression signature is mapped onto a biological process grid or Gene Ontology, to yield a physiological theme pattern. The broadest pattern would include all themes where genes are statistically clustered. A more circumscribed pattern includes, e.g., a subset of themes populated with the strongest-regulated genes, or a subset that is unique with respect to related disorders. Gene expression signatures derived from Gene Ontology and thematic pattern analysis will generally include fewer genes, and are a useful tool for differential diagnosis and screening for actives having very precise and targeted effects.

Systems, Devices, and Computer-Related Aspects of the Invention

Figure 4:
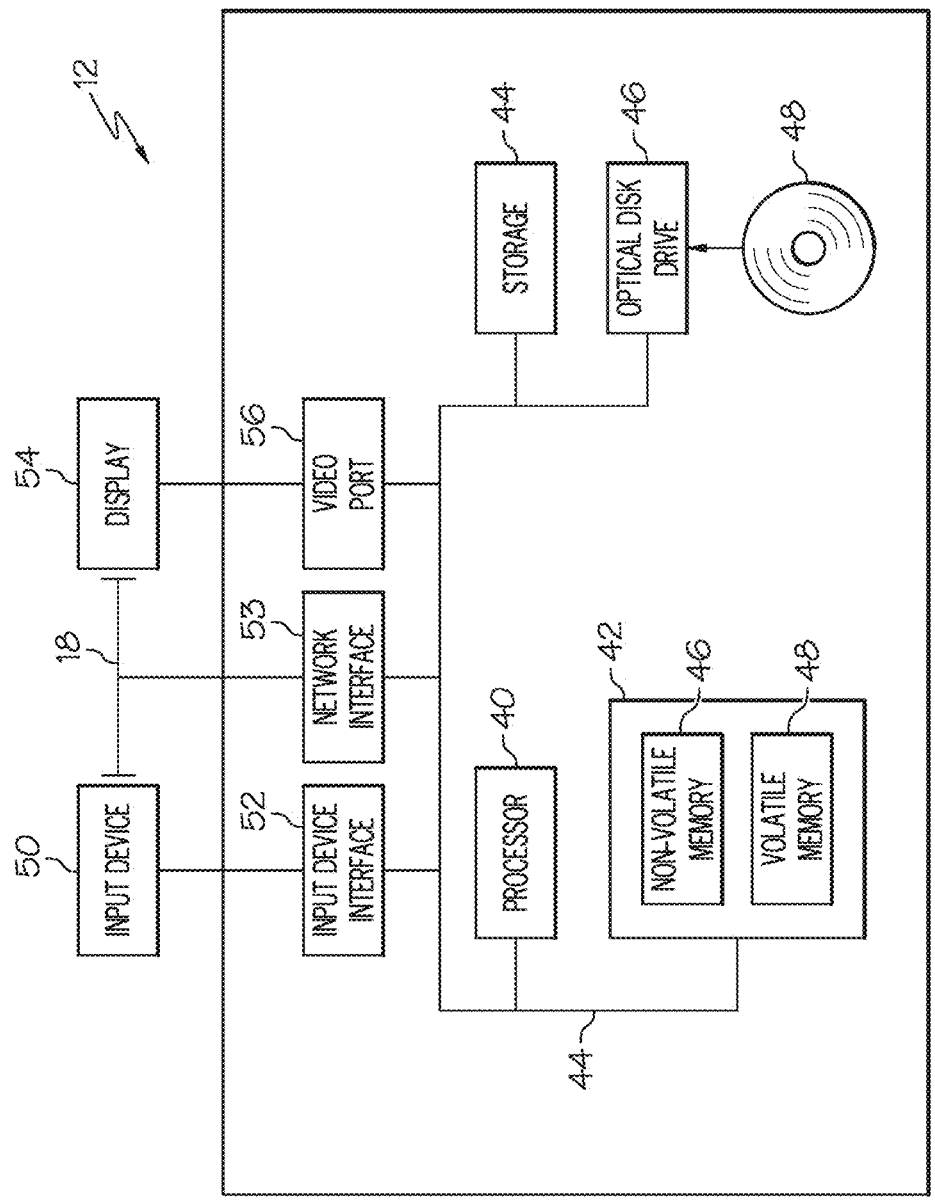
FIG. 4 is a schematic illustration of a programmable computer suitable for use with the invention.
Figure 5:
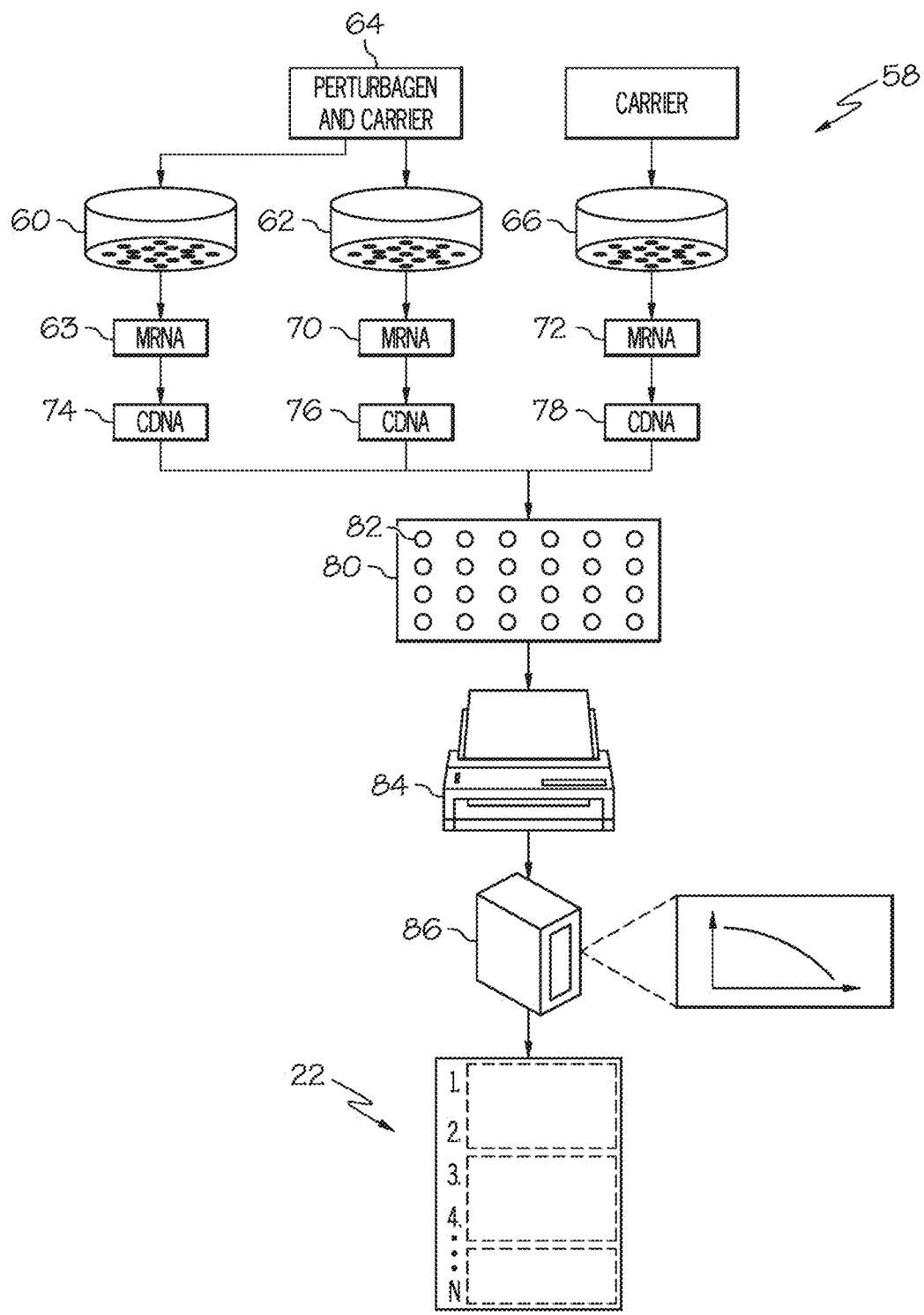
FIG. 5 is a schematic illustration of an exemplary system for measuring gene expression, specifically in the context of generating an instance.

Referring to FIGS. 2, 4 and 5, some examples of systems and devices in accordance with the invention for, e.g., constructing a gene expression signature, identifying connections between skin conditions, identifying relationships between perturbagens and skin homeostasis, identifying skin-active agents, and formulating a skin care composition will now be described. System 10 comprises one or more of computing devices 12, 14, a computer readable medium 16 associated with the computing device 12, and communication network 18.

The computer readable medium 16, which may be provided as a hard disk drive, comprises a digital file 20, such as a database file, comprising a plurality of instances 22, 24, and 26 stored in a data structure associated with the digital file 20. The plurality of instances may be stored in relational tables and indexes or in other types of computer readable media. The instances 22, 24, and 26 may also be distributed across a plurality of digital files, a single digital file 20 being described herein however for simplicity.

The digital file 20 can be provided in wide variety of formats, including but not limited to a word processing file format (e.g., Microsoft Word), a spreadsheet file format (e.g., Microsoft Excel), and a database file format. Some common examples of suitable file formats include, but are not limited to, those associated with file extensions such as *.xls, *.xld, *.xlk, *.xll, *.xlt, *.xlxs, *.dif, *.db, *.dbf, *.accdb, *.mdb, *.mdf, *.cdb, *.fdb, *.csv, *.sql, *.xml, *.doc, *.txt, *.rtf, *.log, *.docx, *.ans, *.pages, *.wps, etc.

Figure 3:
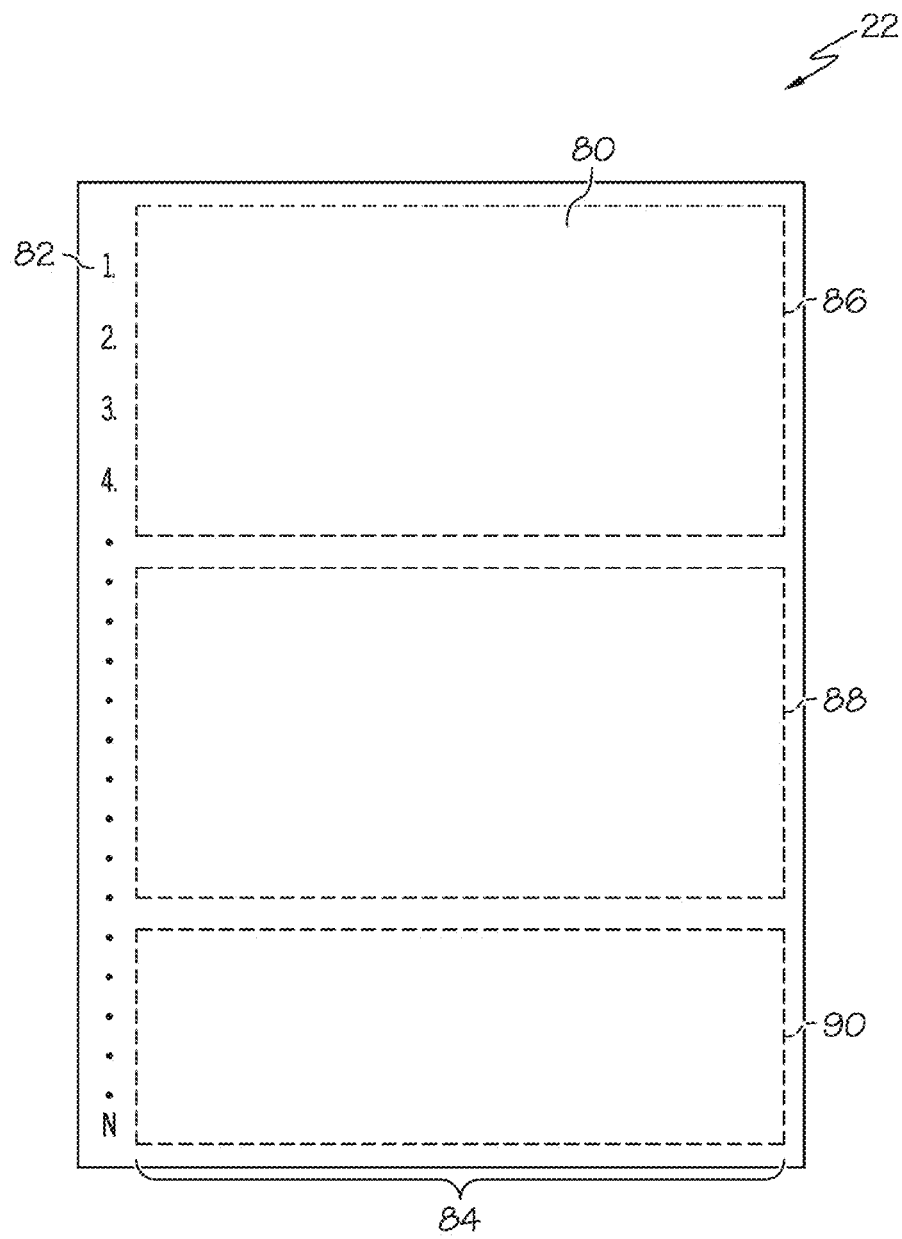
FIG. 3 is a schematic illustration of an instance associated with a computer readable medium of the computer system of FIG. 2.

Referring to FIG. 3, in some embodiments the instance 22 may comprise an ordered listing of microarray probe set IDs, wherein the value of N is equal to the total number of probes on the microarray used in analysis. Common microarrays include Affymetrix GeneChips and Illumina BeadChips. To generate the gene expression profiles, preferred microarrays are those designed for profiling the human genome. One example of Affymetrix chips include, but are not limited to, model Human Genome (HG)-U133 Plus 2.0, such as HG-U133A2.0. Any microarray, regardless of proprietary origin, however, is suitable for use in the context of the invention.

Instances derived from microarray analyses utilizing microarrays (e.g., Affymetrix GeneChips) may comprise an ordered listing of gene probe set IDs. The ordered listing comprises any number of gene probe set IDs, including 2-22,000 IDs or more. The ordered listing may be stored in a data structure of the digital file 20 and the data arranged so that, when the digital file is read by the software application 28, a plurality of character strings are reproduced representing the ordered listing of probe set IDs. While it is preferred that each instance comprises a full list of the probe set IDs, it is contemplated that one or more of the instances may comprise less than all of the probe set IDs of a microarray. It is also contemplated that the instances optionally include other data in addition to or in place of the ordered listing of probe set IDs. For example, an ordered listing of equivalent gene names and/or gene symbols may be substituted for the ordered listing of probe set IDs. Additional data may be stored with an instance and/or the digital file 20. In some embodiments, the additional data is referred to as metadata and can include one or more of cell line identification, batch number, exposure duration, and other empirical data, as well as any other descriptive material associated with an instance ID. The ordered list may also comprise a numeric value associated with each identifier that represents the ranked position of that identifier in the ordered list. In various embodiments, each instance comprises an instance list of rank-ordered identifiers of differentially expressed genes (i.e., genes up-regulated or down-regulated in response to perturbagen exposure).

Referring again to FIGS. 2, 3 and 4, the computer readable medium 16 may also have a second digital file 30 stored thereon. The second digital file 30 comprises one or more lists 32 of microarray probe set IDs (an exemplary identifier) associated with one or more gene expression signatures (e.g., one or more skin condition gene expression signatures). The listing 32 of microarray probe set IDs typically comprises a much smaller list of probe set IDs than the instances of the first digital file 20. In some embodiments, the list comprises between 2 and 1000 probe set IDs. In other embodiments the list comprises greater than about 10, about 50, about 100, about 200, or about 300 and/or less than about 5000, about 2500, about 1000, about 800, about 600, or about 400 probe set IDs. The listing 32 of probe set IDs of the second digital file 30 comprises a list of probe set IDs representing up- and/or down-regulated genes selected to represent one or more skin condition(s) of interest (or cellular response to a particular perturbagen of interest). In some embodiments, a first list may represent the up-regulated genes and a second list may represent the down-regulated genes of the gene expression signature. The listing(s) may be stored in a data structure of the digital file 30 and the data arranged so that, when the digital file is read by the software application 28, a plurality of character strings are reproduced representing the list of probe set IDs. Instead of probe set IDs, equivalent gene names and/or gene symbols (or another nomenclature) may be substituted for a list of probe set IDs. Additional data may be stored with the gene expression signature and/or the digital file 30 and this is commonly referred to as metadata, which may include any associated information, for example, cell line or sample source, and microarray identification. Listings of probe set IDs for an unhealthy skin gene expression signature is set forth in Tables A and B. In some embodiments, one or more gene expression signatures may be stored in a plurality of digital files and/or stored on a plurality of computer readable media. In other embodiments, a plurality of gene expression signatures (e.g., 32, 34) may be stored in the same digital file (e.g., 30) or stored in the same digital file or database that comprises the instances 22, 24, and 26.

The data stored in the first and second digital files may be stored in a wide variety of data structures and/or formats. In some embodiments, the data is stored in one or more searchable databases, such as free databases, commercial databases, or a company's internal proprietary database. The database may be provided or structured according to any model known in the art, such as for example and without limitation, a flat model, a hierarchical model, a network model, a relational model, a dimensional model, or an object-oriented model. In some embodiments, at least one searchable database is a company's internal proprietary database. A user of the system 10 may use a graphical user interface associated with a database management system to access and retrieve data from the one or more databases or other data sources to which the system is operably connected. In some embodiments, the first digital file 20 is provided in the form of a first database and the second digital file 30 is provided in the form of a second database. In other embodiments, the first and second digital files may be combined and provided in the form of a single file.

In some embodiments, the first digital file 20 may include data that is transmitted across the communication network 18 from a digital file 36 stored on the computer readable medium 38. In one embodiment, the first digital file 20 may comprise gene expression data obtained from a cell line (e.g., a fibroblast cell line and/or a keratinocyte cell line) as well as data from the digital file 36, such as gene expression data from other cell lines or cell types, gene expression signatures, perturbagen information, clinical trial data, scientific literature, chemical databases, pharmaceutical databases, and other such data and metadata. The digital file 36 may be provided in the form of a database, including but not limited to Sigma-Aldrich LOPAC collection, Broad Institute C-MAP collection, GEO collection, and Chemical Abstracts Service (CAS) databases.

The computer readable medium 16 (or another computer readable media, such as 16) may also have stored thereon one or more digital files 28 comprising computer readable instructions or software for reading, writing to, or otherwise managing and/or accessing the digital files 20, 30. The computer readable medium 16 may also comprise software or computer readable and/or executable instructions that cause the computing device 12 to perform one or more steps of the methods of the invention, including for example and without limitation, the step(s) associated with comparing a gene expression signature stored in digital file 30 to instances 22, 24, and 26 stored in digital file 20. In some embodiments, the one or more digital files 28 may form part of a database management system for managing the digital files 20, 28. Non-limiting examples of database management systems are described in U.S. Pat. Nos. 4,967,341 and 5,297,279.

The computer readable medium 16 may form part of, or otherwise be connected to, the computing device 12. The computing device 12 can be provided in a wide variety of forms, including but not limited to, any general or special purpose computer such as a server, a desktop computer, a laptop computer, a tower computer, a microcomputer, a mini computer, and a mainframe computer. While various computing devices may be suitable for use with the invention, a generic computing device 12 is illustrated in FIG. 4. The computing device 12 may comprise one or more components selected from a processor 40, system memory 42, and a system bus 44. The system bus 44 provides an interface for system components including but not limited to the system memory 42 and processor 40. The system bus 36 can be any of several types of bus structures that may further interconnect to a memory bus (with or without a memory controller), a peripheral bus, and a local bus using any of a variety of commercially available bus architectures. Examples of a local bus include an industrial standard architecture (ISA) bus, a microchannel architecture (MSA) bus, an extended ISA (EISA) bus, a peripheral component interconnect (PCI) bus, a universal serial (USB) bus, and a small computer systems interface (SCSI) bus. The processor 40 may be selected from any suitable processor, including but not limited to, dual microprocessor and other multi-processor architectures. The processor executes a set of stored instructions associated with one or more program applications or software.

The system memory 42 can include non-volatile memory 46 (e.g., read only memory (ROM), erasable programmable read only memory (EPROM), electrically erasable programmable read only memory (EEPROM), etc.) and/or volatile memory 48 (e.g., random access memory (RAM)). A basic input/output system (BIOS) can be stored in the non-volatile memory 38, and can include the basic routines that help to transfer information between elements within the computing device 12. The volatile memory 48 can also include a high-speed RAM such as static RAM for caching data.

The computing device 12 may further include a storage 44, which may comprise, for example, an internal hard disk drive (HDD, e.g., enhanced integrated drive electronics (EIDE) or serial advanced technology attachment (SATA)) for storage. The computing device 12 may further include an optical disk drive 46 (e.g., for reading a CD-ROM or DVD-ROM 48). The drives and associated computer-readable media provide non-volatile storage of data, data structures and the data architecture of the present invention, computer-executable instructions, and so forth. For the computing device 12, the drives and media accommodate the storage of any data in a suitable digital format. Although the description of computer-readable media above refers to an HDD and optical media such as a CD-ROM or DVD-ROM, it should be appreciated by those skilled in the art that other types of media which are readable by a computer, such as Zip disks, magnetic cassettes, flash memory cards, cartridges, and the like may also be used, and further, that any such media may contain computer-executable instructions for performing the methods of the invention.

A number of software applications can be stored on the drives 44 and volatile memory 48, including an operating system and one or more software applications, which implement, in whole or part, the functionality and/or methods described herein. It is to be appreciated that the embodiments can be implemented with various commercially available operating systems or combinations of operating systems. The central processing unit 40, in conjunction with the software applications in the volatile memory 48, may serve as a control system for the computing device 12 that is configured to, or adapted to, implement the functionality described herein.

A user enters commands and information into the computing device 12 through one or more wired or wireless input devices 50, such as, for example, a keyboard, a pointing device (e.g., a mouse (not illustrated)), or a touch screen. These and other input devices are often connected to the central processing unit 40 through an input device interface 52 that is coupled to the system bus 44 but can be connected by other interfaces, such as a parallel port, an IEEE 1394 serial port, a game port, a universal serial bus (USB) port, an IR interface, etc. The computing device 12 may drive a separate or integral display device 54, which may also be connected to the system bus 44 via an interface, such as a video port 56.

The computing devices 12, 14 may operate in a networked environment across network 18 using a wired and/or wireless network communications interface 58. The network interface port 58 can facilitate wired and/or wireless communications. The network interface port can be part of a network interface card, network interface controller (NIC), network adapter, or LAN adapter. The communication network 18 can be a wide area network (WAN) such as the Internet, or a local area network (LAN). The communication network 18 can comprise a fiber optic network, a twisted-pair network, a T1/E1 line-based network or other links of the T-carrier/E carrier protocol, or a wireless local area or wide area network (operating through multiple protocols such as ultra-mobile band (UMB), long term evolution (LTE), etc.). Additionally, communication network 18 can comprise base stations for wireless communications, which include transceivers, associated electronic devices for modulation/demodulation, and switches and ports to connect to a backbone network for backhaul communication such as in the case of packet-switched communications.

In one aspect, the invention provides a system for evaluating the influence of perturbagens on skin homeostasis, thereby potentially connecting one or more perturbagens with one or more biological processes (e.g., elucidating a positive or negative relationship between a perturbagen and phenotype). The system comprises at least one computer readable medium as described above, having stored thereon a plurality of instances and an unhealthy skin gene expression signature. Each instance comprises an instance list of rank-ordered identifiers of differentially expressed genes, and the unhealthy skin gene expression signature comprises one or more gene expression signature lists of identifiers representing differentially expressed genes associated with unhealthy skin. The system further comprises a programmable computer comprising computer-readable instructions that cause the programmable computer to execute one or more of the following: (i) accessing the plurality of instances and the unhealthy skin gene expression signature stored on the computer readable medium; (ii) comparing the unhealthy skin gene expression signature to the plurality of the instances, wherein the comparison comprises comparing each identifier in the gene expression signature list with the position of the same identifier in the instance list for each of the plurality of instances; and (iii) assigning a connectivity score to each of the plurality of instances.

Optionally, the system further comprises a microarray scanner for receiving a biological sample; and a second programmable computer for transmitting gene expression data from the scanner to the first programmable computer. The biological sample comprises gene expression products, as described further herein. Alternatively or in addition, the system further comprises an array of perturbagens for application to human skin cells.

Evaluating the Influence of Perturbagens on Skin Homeostasis and Commonalities Between Biological Conditions The gene expression signature described herein is useful for identifying connections between perturbagens and skin homeostasis, i.e., determining whether a perturbagen modulates one or more aspects of skin health. Put another way, the invention provides a method for evaluating the influence of one or more perturbagens on, e.g., cutaneous regulation, skin barrier structure and function, transepidermal water loss, moisturization, and skin appearance. For example, the unhealthy skin gene expression signature is useful for identifying agents that improve and/or maintain skin health, as well as evaluating candidate skin-active agents for activity against one or more skin conditions of interest (e.g., one or more of acne, atopic dermatitis, dandruff, psoriasis, and eczema). Indeed, the materials and methods of the invention lend themselves to screening tens to hundreds of thousands of candidate active agents in silico to identify lead candidates for further evaluation using, e.g., the in vitro and ex vivo methods described herein. In this regard, the invention includes systems and methods utilizing connectivity mapping to predict effectiveness of potential skin-active agents for reducing or ameliorating the symptoms associated with wide variety of skin disorders, including acne, atopic dermatitis, dandruff, psoriasis, eczema, and any combination of the foregoing. Connectivity mapping (C-map) discovers functional connections between gene expression associated with a phenotype and cellular responses to perturbagens. Connectivity mapping is described in detail herein and further described in, e.g., Hughes et al., Cell, 102, 109-126 (2000); and Lamb et al., Science, 313, 1929-35 (2006).

The invention provides a method for evaluating the influence of perturbagens on skin homeostasis. The method comprises querying a data architecture of stored skin instances, each skin instance being associated with a perturbagen, with an unhealthy skin gene expression signature. The querying comprises comparing the unhealthy skin gene expression signature to each stored skin instance (i.e., comparing each identifier in the gene expression signature list of the unhealthy gene signature with the position of the same identifier in each instance list). Optionally, the method comprises querying a data architecture of stored skin instances associated with perturbagens that influence cell signaling, system development, epidermis development, immune system process, and inflammation. Also optionally, the comparison of the unhealthy skin gene expression signature to each stored skin instance comprises assigning a connectivity score to each of a plurality of instances. In various aspects, the method further comprises identifying a skin instance having a negative connectivity score (which represents a negative correlation between the unhealthy skin gene expression signature and instance) and/or identifying a skin instance having a positive connectivity score (which represents a positive correlation between the unhealthy skin gene expression signature and instance). The method also comprises formulating a skin care composition comprising a dermatologically acceptable carrier and the perturbagen associated with the identified skin instance, in some embodiments.

A method for formulating a skin care composition also is included in the invention. The method comprises accessing a plurality of instances stored on at least one computer readable medium. Each instance is associated with a perturbagen (and optionally a skin cell type) and comprises an ordered list of a plurality of identifiers representing up-regulated genes and down-regulated genes. The method further comprises accessing at least one unhealthy skin gene expression signature stored on the computer readable medium. The unhealthy skin gene expression signature comprises one or more gene expression signature lists comprising a plurality of identifiers representing a plurality of up-regulated genes and a plurality of down-regulated genes associated with acne, atopic dermatitis, eczema, psoriasis, and dandruff. The unhealthy skin gene expression signature is compared to the plurality of the instances, wherein the comparison comprises comparing each identifier in the one or more gene expression signature lists with the position of the same identifier in the ordered lists for each of the plurality of instances, and a connectivity score is assigned to each of the plurality of instances. The method further comprises formulating a skin care composition comprising a dermatologically acceptable carrier and at least one perturbagen, wherein the connectivity score of the instance associated with the at least one perturbagen is negative (i.e., there is a negative correlation between the instance and the query gene expression signature).

Additionally, the invention provides a method of identifying commonalities between one or more biological conditions of interest and unhealthy skin. In this respect, the instances of the method described above are replaced with one or more gene expression profiles of one or more biological conditions (other than acne, atopic dermatitis, eczema, psoriasis, and dandruff). The biological condition is, in various embodiments, not a skin condition (i.e., a disorder that primarily manifests in the skin). The method allows detection and analysis of common features of seemingly disparate biological conditions, thereby providing valuable insight into potential therapeutic targets.

Thus, in one aspect, the method comprises querying a data architecture of stored gene expression profiles of one or more biological conditions with an unhealthy skin gene expression signature. The querying comprises comparing the unhealthy skin gene expression signature to each stored gene expression profile (i.e., comparing each identifier in the gene expression signature list of the unhealthy gene signature with the position of the same identifier in each gene expression profile of the biological condition(s)). Optionally, the comparison of the unhealthy skin gene expression signature to each stored gene expression profile comprises assigning a connectivity score to one or more of the biological conditions.

Generating Instances, Ordering Data

In some embodiments, the inventive methods comprise populating at least the first digital file 20 with a plurality of instances (e.g., 22, 24, 26) comprising data derived from a plurality of gene expression profiling experiments, wherein one or more of the experiments comprise exposing, for example, keratinocyte cells (or other skin cells such as human skin equivalent cultures or ex vivo cultured human skin) to at least one perturbagen. For simplicity of discussion, the gene expression profiling discussed hereafter will be in the context of a microarray experiment. An exemplary method of generating an instance is illustrated in FIG. 5. In one embodiment, an instance consists of the rank ordered data for all of the probe sets on an Affymetrix HG-U133A2.0 GeneChip, wherein each probe on the chip has a unique probe set IDentifier. The probe sets are rank ordered by the fold-change level of gene expression detected relative to controls in the same C-map batch (single instance/average of controls). The probe set identifiers are rank-ordered to reflect the most up-regulated to the most down-regulated.

Notably, even for non-differentially regulated genes, the signal values for a particular probe set are unlikely to be identical for a gene expression profile (e.g., associated with an instance or associated with a biological condition of interest) and a control profile. A fold-change different from 1 is calculated and can be used for comprehensive rank ordering. In accordance with methods disclosed by Lamb et al. (2006), data are adjusted using 2 thresholds to minimize the effects of genes that may have very low, noisy signal values. The thresholding is preferably performed before rank ordering. An example for illustrative purposes includes a process wherein a first threshold is set at 20. If the signal for a probe set is below 20, it is adjusted to 20. Ties for ranking are broken with a second threshold wherein the fold changes are recalculated and any values less than 2 are set to 2. For any remaining ties, the order depends on the sorting algorithm used, but is essentially random. The probe sets in the middle of the list do not meaningfully contribute to an actual connectivity score.

The rank ordered data are stored as an instance or a gene expression profile. The probes may be sorted into a list according to the level of gene expression regulation detected, wherein the list progresses from up-regulated to marginal or no regulation to down-regulated, and this rank ordered listing of probe IDs is stored as an instance (e.g., 22 in FIG. 5) in the first digital file 20. Referring to FIG. 3, the data associated with an instance (or gene expression profile associated with a biological disorder of interest) comprises the probe ID 80 and a value 82 representing its ranking in the list (e.g., 1, 2, 3, 4 . . . N, where N represents the total number of probes on the microarray). The ordered list 84 may generally comprise approximately three groupings of probe IDs: a first grouping 86 of probe IDs associated with up-regulated genes, a second group 88 of probe IDs associated with genes with marginal regulation or no detectable signal or noise, and a third group 90 of probe IDs associated with down-regulated genes. The most up-regulated genes are at or near the top of the list 84 and the most down-regulated genes are at or near the bottom of the list 84. The groupings are shown for illustration, but the lists for each instance may be continuous and the number of regulated genes will depend on, e.g., the strength of the effect of the perturbagen associated with the instance. Other arrangements within the list 84 may be provided. For example, the probe IDs associated with the down-regulated genes may be arranged at the top of the list 84. This instance data may also further comprise metadata such as perturbagen identification, perturbagen concentration, cell line or sample source, and microarray identification.

In some embodiments, one or more instances (or gene expression profiles) comprise at least about 1,000, 2,500, 5,000, 10,000, or 20,000 identifiers and/or less than about 30,000, 25,000, or 20,000 identifiers. In some embodiments, a database comprises at least about 50, 100, 250, 500, or 1,000 instances and/or less than about 50,000, 20,000, 15,000, 10,000, 7,500, 5,000, or 2,500 instances. Replicates of an instance may be created, and the same perturbagen may be used to derive a first instance from a particular cell type (e.g., keratinocyte cells) and a second instance from another target cell type or biological sample (e.g., fibroblasts, melanocytes, or complex tissue, such as, ex vivo human skin).

Comparing Gene Expression Signature(s) to Instances

Figure 6:
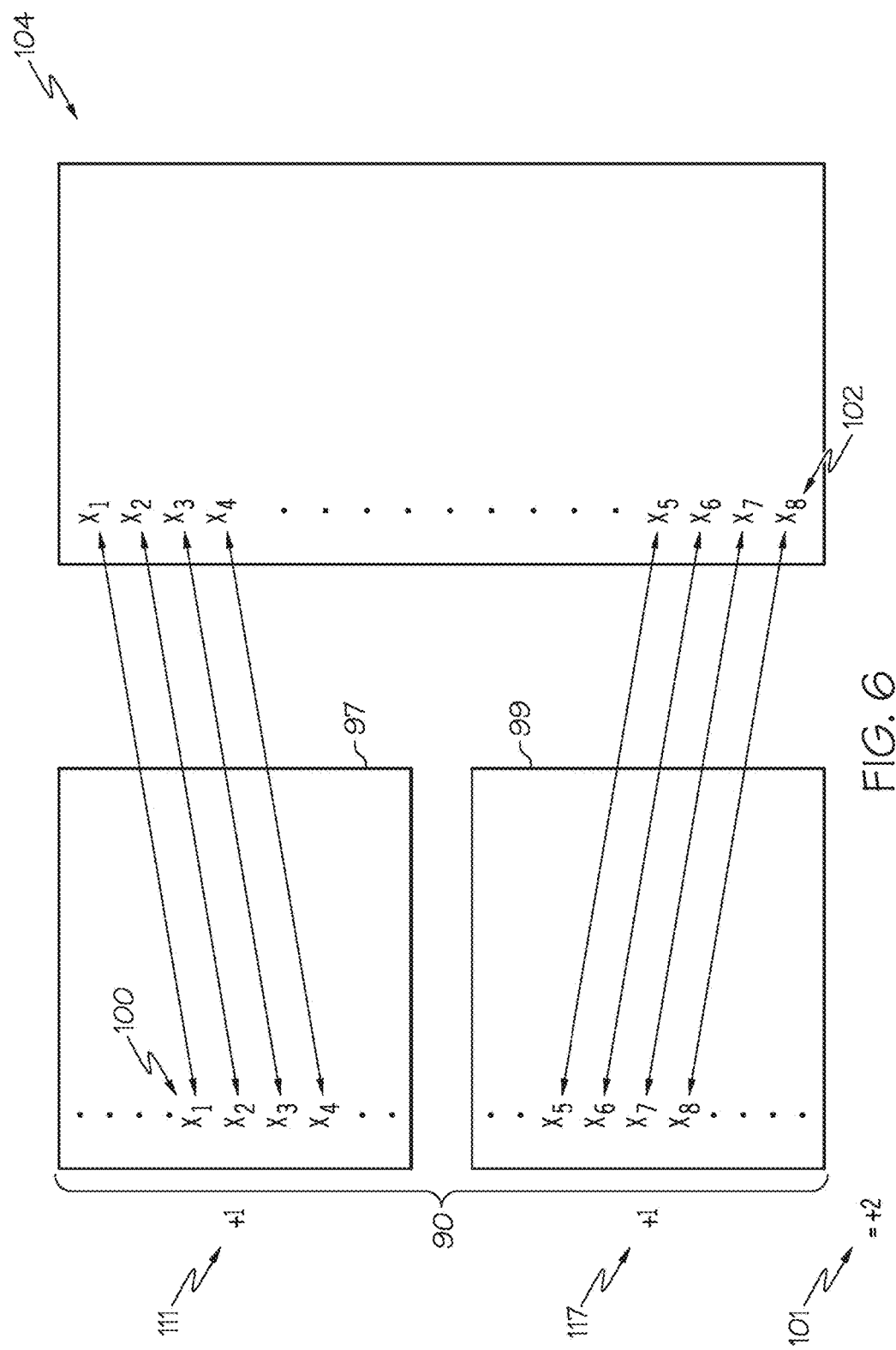
FIG. 6 is a schematic illustration of a comparison between a gene expression signature and an instance, wherein there is a positive correlation between the lists.
Figure 7:
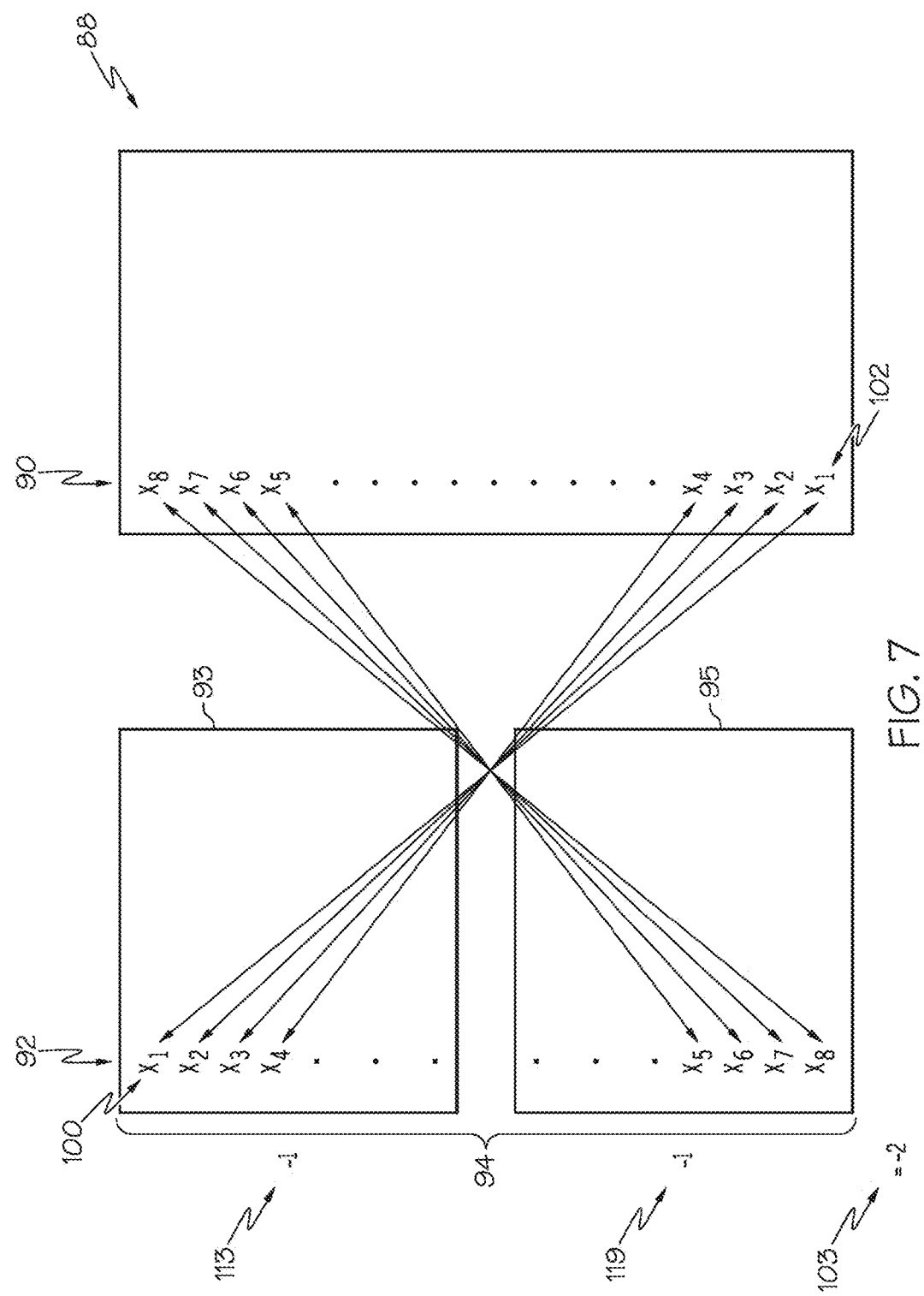
FIG. 7 is a schematic illustration of a comparison between a gene expression signature and an instance, wherein there is a negative correlation between the lists.
Figure 8:
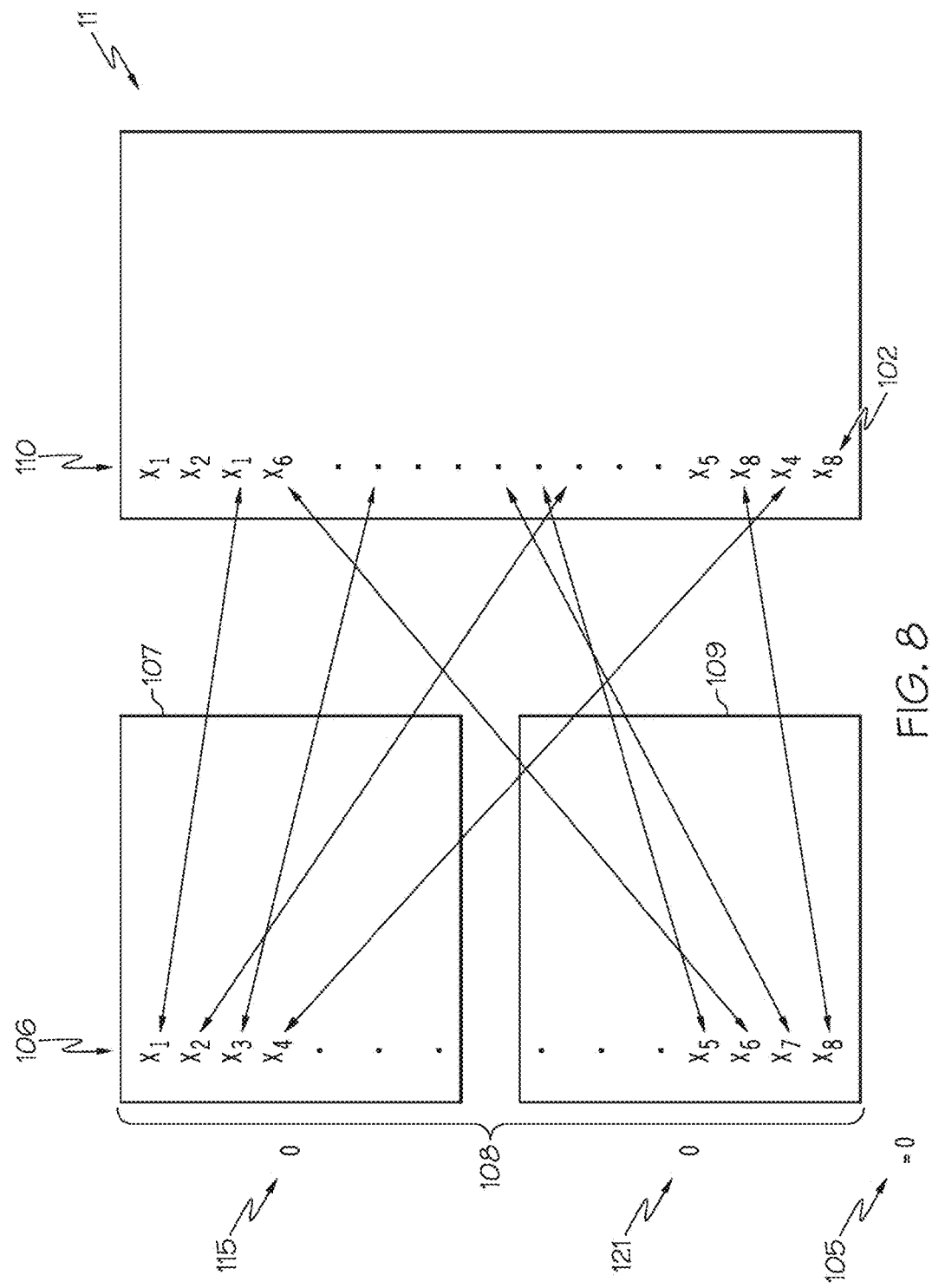
FIG. 8 is a schematic illustration of a comparison between a gene expression signature and an instance, wherein there is a neutral correlation between the lists.

Referring to FIG. 6 and FIG. 7, an exemplary method for querying instances with one or more gene expression signatures will now be described. Broadly, the method comprises querying a data architecture of stored instances (e.g., skin instances) with one or more gene signatures (e.g., an unhealthy skin gene expression signature), and applying a statistical method to determine how strongly the gene expression signature genes match the regulated genes in an instance. Positive connectivity occurs when the genes in the up-regulated gene expression signature list are enriched among the up-regulated genes in an instance and the genes in the down-regulated gene expression signature list are enriched among the down-regulated genes in an instance. On the other hand, if the up-regulated genes of the gene expression signature are predominantly found among the down-regulated genes of the instance, and vice versa, this is scored as negative connectivity. FIG. 6 schematically illustrates an extreme example of a positive connectivity between signature 90 and the instance 104 comprising the probe IDs 102, wherein the probe IDs of the instance are ordered from most up-regulated to most down-regulated. In this example, the probe IDs 100 (e.g., $X_1$, $X_2$ $X_3$, $X_4$, $X_5$, $X_6$, $X_7$, $X_8$) of the gene signature 90, comprising an up list 97 and a down list 99, have a one to one positive correspondence with the most up-regulated and down-regulated probe IDs 102 of the instance 104, respectively. Similarly, FIG. 7 schematically illustrates an extreme example of a negative connectivity between signature 94 and the instance 88 comprising the probe IDs 90, wherein the probe IDs of the instance are ordered from most up-regulated to most down-regulated. In this example, the probe IDs of the up list 93 (e.g., $X_1$, $X_2$ $X_3$, $X_4$) correspond exactly with the most down-regulated genes of the instance 88, and the probe IDs of the down list 95 (e.g., $X_5$, $X_6$, $X_7$, $X_8$) correspond exactly to the most up-regulated probe IDs of the instance 88. FIG. 8 schematically illustrates an extreme example of neutral connectivity, wherein there is no consistent enrichment of the up- and down-regulated genes of the signature among the up- and down-regulated genes of the instance, either positive or negative. Hence the probe IDs 106 (e.g., $X_1$, $X_2$ $X_3$, $X_4$, $X_5$, $X_6$, $X_7$, $X_8$) of a gene signature 108 (comprising an up list 107 and a down list 109) are scattered with respect to rank with the probe IDs 110 of the instance 112, wherein the probe IDs of the instance are ordered from most up-regulated to most down-regulated. While the above embodiments illustrate process where the gene signature comprises both an "up list" and a "down list" representative of the most significantly up- and down-regulated genes of a skin condition, it is contemplated that the gene signature may comprise only an up list or a down list when the dominant biology associated with a condition of interest shows gene regulation in predominantly one direction.

In some embodiments, the connectivity score is a combination of an up-score and a down-score, wherein the up-score represents the correlation between the up-regulated genes of a gene expression signature and an instance and the down-score represents the correlation between the down-regulated genes of a gene expression signature and an instance. The up-score and down-score have, for example, values between +1 and −1. For an up-score (and down-score), a high positive value indicates that the corresponding perturbagen of an instance induced expression of genes corresponding to microarray probes specific for the up-regulated (or down-regulated) genes of the gene expression signature. A high negative value indicates that the corresponding perturbagen associated with the instance repressed (down-regulated) the expression of genes associated with microarray probes specific for the up-regulated (or down-regulated) genes of the gene signature. The up-score can be calculated by comparing each identifier of an up list of a gene expression signature comprising the up-regulated genes (e.g., Table A and lists 93, 97, and 107 of FIGS. 6-8) to an ordered instance list while the down-score can be calculated by comparing each identifier of a down list of a gene signature comprising the down-regulated genes (see, e.g., Table B and down lists 95, 99, and 109 of FIGS. 6-8) to an ordered instance list. In these embodiments, the gene expression signature comprises the combination of the up list and the down list.

In some embodiments, the connectivity score value may range from +2 (greatest positive connectivity) to −2 (greatest negative connectivity), wherein the connectivity score (e.g., 101, 103, and 105) is the combination of the up score (e.g., 111, 113, 115) and the down score (e.g., 117, 119, 121) derived by comparing each identifier of a gene signature to the identifiers of an ordered instance list. In other embodiments the connectivity range may be between +1 and −1. Examples of the scores are illustrated in FIGS. 6-8 as reference numerals 101, 103, 105, 111, 113, 115, 117, 119, and 121. The strength of matching between a gene expression signature and an instance represented by the up scores and down scores and/or the connectivity score may be derived by one or more approaches known in the art and include, but are not limited to, parametric and non-parametric approaches. Examples of parametric approaches include Pearson correlation (or Pearson r) and cosine correlation. Examples of non-parametric approaches include Spearman's Rank (or rank-order) correlation, Kendall's Tau correlation, and the Gamma statistic. Optionally, in order to eliminate a requirement that all profiles be generated on the same microarray platform, a non-parametric, rank-based pattern matching strategy based on the Kolmogorov-Smirnov statistic (see M. Hollander et al. "*Nonparametric Statistical Methods*"; Wiley, New York, ed. 2, 1999)(see, e.g., pp. 178-185) is used. Where all expression profiles are derived from a single technology platform, similar results may be obtained using conventional measures of correlation, for example, the Pearson correlation coefficient.

In specific embodiments, the methods and systems of the invention employ the nonparametric, rank-based pattern-matching strategy based on the Kolmogorov-Smirnov statistic, which has been refined for gene profiling data and is known as Gene Set Enrichment Analysis (GSEA) (see, e.g., Lamb et al. 2006 and Subramanian, A. et al. (2005) *Proc. Natl. Acad Sci U.S.A*, 102, 15545-15550). For each instance, a down score is calculated to reflect the match between the down-regulated genes of the query and the instance, and an up score is calculated to reflect the correlation between the up-regulated genes of the query and the instance. In certain embodiments the down-score and up-score each may range between −1 and +1. The combination represents the strength of the overall match between the query signature and the instance.

The combination of the up-score and down-score is used to calculate an overall connectivity score for each instance, and in embodiments where up- and down-score ranges are set between −1 and +1, the connectivity score ranges from −2 to +2, and represents the strength of match between a query gene expression signature and the instance. The sign of the overall score is determined by whether the instance links positivity or negatively to the signature. Positive connectivity occurs when the perturbagen associated with an instance tends to up-regulate the genes in the up list of the signature and down-regulate the genes in the down list. Conversely, negative connectivity occurs when the perturbagen tends to reverse the up- and down-signature gene expression changes. The magnitude of the connectivity score is the sum of the absolute values of the up and down scores when the up and down scores have different signs. A high positive connectivity score predicts that the perturbagen will tend to induce the condition associated with the query gene expression signature, and a high negative connectivity score predicts that the perturbagen will tend to reverse the condition associated with the query gene expression signature. A zero score is assigned where the up- and down-scores have the same sign, indicating that a perturbagen did not have a consistent impact on the condition gene expression signature (e.g., up-regulating both the up and down lists).

According to Lamb et al. (2006), there is no standard for estimating statistical significance of connections observed. The power to detect connections may be greater for compounds with many replicates. Replicating in this context means that the same perturbagen is profiled multiple times. Profiling a perturbagen multiple times in each batch reduces batch to batch variation. Since microarray experiments tend to have strong batch effects, instances are optionally replicated in different batches (i.e., experiments) to increase confidence that connectivity scores are meaningful and reproducible.

Each instance may be rank ordered according to its connectivity score to the query gene expression signature, and the resulting rank ordered list displayed to a user using any suitable software and computer hardware allowing for visualization of data.

In some embodiments, the methods may comprise identifying from the displayed rank-ordered list of instances (i) the one or more perturbagens associated with the instances of interest (thereby correlating activation or inhibition of a plurality of genes listed in the query signature to the one or more perturbagens); (ii) the differentially expressed genes associated with any instances of interest (thereby correlating such genes with the one or more perturbagens, the skin tissue condition of interest, or both); (iii) the cells associated with any instance of interest (thereby correlating such cells with one or more of the differentially expressed genes, the one or more perturbagens, and the skin tissue condition of interest); or (iv) combinations thereof. The perturbagen(s) associated with an instance may be identified from the metadata stored in the database for that instance. However, one of skill in the art will appreciate that perturbagen data for an instance may be retrievably stored in and by other means. Because the identified perturbagens statistically correlate to activation or inhibition of genes listed in the query gene expression signature, and because the query gene expression signature is a proxy for a biological condition (e.g., a plurality of skin conditions of interest), the identified perturbagens may be candidates for new cosmetic agents, new uses of known cosmetic agents, or to validate known agents for known uses.

Characterizing Perturbagen Activity in Models of Skin Conditions

In some embodiments, the inventive methods include characterizing activity of a perturbagen associated with an instance (i.e., a candidate skin-active agent) in one or more assays to validate the activity of the agent and usefulness as a skin care agent. A great challenge in the identification of new skin care actives is the development of in vitro models that are predictive of clinical efficacy. The challenge of developing predictive in vitro and ex vivo models for skin conditions is complicated by the fact that the triggers of many skin conditions and the underlying biology are poorly understood. The transcriptomic profiling of a plurality of skin conditions described herein provided many new insights into in vitro and ex vivo assays that recapitulate the common key features of multiple skin conditions in vivo. In this regard, in various embodiments, the invention further includes characterizing the activity of a perturbagen in one or more assays selected from the group consisting of an inflammation simulation assay, an epidermal differentiation assay, an epithelial cell proliferation assay, and lipid metabolism assay. Optionally, the method comprises characterizing the activity of the perturbagen in an inflammation simulation assay, an epidermal differentiation assay, an epithelial cell proliferation assay, and lipid metabolism assay. The method, in various aspects, additionally comprises characterizing activity of the perturbagen in an ex vivo skin model of inflammation and/or a three-dimensional organotypic model of inflammation.

The invention provides a coherent, tiered system of assays for characterizing the influence of a candidate skin-active agent on skin homeostasis. For example, in one embodiment, the method comprises characterizing the activity of the perturbagen in a cell-based assay, characterizing the activity of the perturbagen in an ex vivo tissue assay, and characterizing the activity of the perturbagen in vivo. The cell-based assay is optionally selected from the group consisting of an inflammation assay, an epidermal differentiation assay, an epithelial cell proliferation assay, and lipid metabolism assay, and any combination of the foregoing. The ex vivo tissue assay is optionally a skin model of inflammation and/or a three-dimensional organotypic model of inflammation.

Exemplary inflammation simulation, epidermal differentiation, epithelial cell proliferation, and lipid metabolism assays are described herein. Cell cultures or skin models suitable for studying inflammation, differentiation, proliferation, and lipid metabolism include, but are not limited to, organotypic culture, NHEK or tert-keratinocytes cultures (including vitamin C/Serum NHEK system), and pig or human explants. Many tissue models are available commercially, including the MatTek Corp. NHEK-based EpiDerm™ systems. Ex vivo skin models often comprise skin (e.g., human skin) surgically removed from a subject and cultured in a manner that mimics in vivo conditions (e.g., circulation). Ex vivo skin models using human skin are advantageous because the model includes a functional, fully formed stratum corneum barrier; appropriate tissue architecture; and most (if not all) of the full complement of cell types present within human skin. Ex vivo human skin models also largely respond to certain challenges in a similar manner to in vivo skin. Three-dimensional organotypic models include keratinocyte-derived three dimensional epithelium which develops when keratinocytes are cultured on an inert medium (e.g., collagen gel) and raised to the air-liquid interface in a tissue culture dish. Three-dimensional organotypic models are responsive to inflammatory challenge and differentiate in a manner that is very similar in vivo skin. Suitable ex vivo models and assay conditions are described in U.S. Patent Application No. 61/683,452, filed Aug. 15, 2012, which is hereby incorporated by reference.

In various aspects, the cells/explants are treated with one or a combination of perturbagens which induce a physiological theme pattern for the skin conditions. The combination of IL-22/17 is a very good means for simulating an inflammatory environment that resembles the pathology associated with a number of skin conditions, including dandruff, acne, dermatitis, eczema, and psoriasis. Indeed, the combination of IL-22 and IL-17 influences many biological processes in the same manner as observed in, e.g., dandruff. For example, dandruff suffers exhibit increased keratinocyte differentiation, decreased apoptosis regulation; increased responses to inflammation, biotic stimulus, hormone stimulus, and wounding; and decreased ketone metabolism, lipid biosynthesis, and steroid biosynthesis. Skin cell exposure to IL-22 and IL-17 induced similar biological responses. Additionally, in vitro simulations of dandruff with IL-22 and IL-17 produced cascades of gene expression that strongly resemble the unhealthy skin gene expression pattern described herein. Thus, in one aspect, the invention includes characterizing perturbagen activity in an ex vivo model of skin inflammation, which comprises a mammalian skin sample comprising an epidermal layer and a dermal layer wherein inflammation is induced by delivering an effective amount of a stimulant selected from the group consisting of IL-17, IL-22, IL-1b, and combinations thereof, to the mammalian skin sample.

The effect of a perturbagen on, e.g., inflammation, epidermal differentiation, epithelial cell proliferation, and/or lipid metabolism is determined by examining any of a number of endpoints, including, but not limited to, lipid content (e.g., determined by Oil Red O Staining/TLC evaluation of major subcutaneous lipid classes), production of relevant lipid biosynthetic enzymes, cornified envelope formation (e.g., via colorimetric determination of covalently cross-linked envelope proteins), production of squamous differentiation markers, presence of Retinoic acid Metabolism Blocking Agents (RAMBA) (e.g., via detection of human CYP3A4 inhibition), basal cell proliferation (e.g., detected using PCNA, Ki67 or BrdU staining or by observing thickness of viable epidermis), pro-inflammatory cytokine production (e.g., via measuring IL-8 release or NF-kB activity), and/or anti-inflammatory cytokine production (e.g., via measuring IL-10 production). Alternatively or in addition, barrier homeostasis biomarker (e.g., filaggrin, involucrin, serine palmitoyl transferase I and II, transglutaminase I, acid sphingomyelinase, beta glucocerebrosidase, glucosyl ceramide synthase, ceramide kinase) gene expression is detected and/or quantified.

In various embodiments, the activity of a perturbagen is compared to a benchmark. For example, in a lipid metabolism assay, cholesterol, free fatty acid, and/or ceramide produced in skin cells (e.g., keratinocytes) exposed to the perturbagen is quantified. A perturbagen that mediates a level of production of cholesterol, free fatty acid, ceramide, or any combination thereof, that is equal to or greater than the level of production observed in matched cells (i.e., the same cell type, cultured under similar conditions) treated with calcium, is a lipid metabolism modulator, and is a candidate skin-active agent. An exemplary epidermal differentiation assay compares cornified envelope formation by keratinocytes exposed to a perturbagen or a known skin cell differentiator. For example, cells are exposed to a perturbagen, and the amount of cross-linked envelope proteins produced by the cells is quantified and compared to the amount of cross-linked envelope proteins produced by cells treated with Anthralin. A perturbagen that mediates a level of cross-linked protein production that is equal to, or greater than, the level of cross-linked envelope protein production mediated by Anthralin, is a differentiation modulator, and is a candidate skin-active agent.

An exemplary benchmark for a cell proliferation assay and an inflammation assay is clobetasol, a corticosteroid used to treat, e.g., eczema and psoriasis. Perturbagen activity need not be compared to a benchmark active, however. In this regard, a perturbagen that mediates a statistically significant level of suppression (e.g., $p<0.05$ from a t-test) of cell proliferation compared to a negative control (e.g., cell proliferation in the absence of a proliferation inhibitor, including cell proliferation observed without an exogenous initiator of proliferation and cell proliferation achieved in response to an exogenous proliferation trigger (such as IL-17 and IL-22)) is considered a candidate skin-active agent. The level of cell proliferation mediated by clobetasol is a useful reference for cell proliferation assays in the context of the invention. Perturbagens that suppress cell proliferation to a degree comparable to, or greater than, the level of suppression mediated by clobetasol also are candidate skin-active agents. In an inflammation assay, cells challenged by, e.g., IL-22/IL-17 are exposed to a perturbagen, and IL-8 is measured as a surrogate for inflammation. A statistically significant reduction or suppression of IL-8 mediated by the perturbagen, compared to a negative control (e.g., inflammation observed in the absence of the perturbagen), indicates that the perturbagen is an anti-inflammatory agent, and is a candidate skin-active agent. If desired, the activity of the perturbagen is compared to that of clobetasol; a perturbagen that mediates a level of suppression of IL-8 that is equal to, or greater than, clobetasol is also considered a candidate skin-active agent.

The methods described herein are amenable to automation and, as such, may be formatted as a high-throughput method for characterizing the activity of the perturbagen. Use of automation equipment allows identification of candidate skin-active agents and rapid characterization of the activity of multiple candidates (e.g., hundreds or thousands of candidates) in parallel, which is contemplated herein. Indeed, the methods of the invention are appropriate for large scale screening of libraries of potential active agents.

Compositions and Personal Care Products

Generally, skin-active agents are applied in accordance with cosmetic compositions and formulation parameters well-known in the art. Various methods of treatment, application, regulation, or improvement may utilize skin care compositions comprising skin-active agents identified according to the inventive methods. An "effective amount" of a skin-active agent is an amount sufficient to achieve the desired biological effect. An effective amount will vary with the particular skin condition(s) being treated, the particular agent used, the age and physical condition of the subject, and the duration of the treatment period. It may be advantageous to administer multiple applications of a skin-active agent over a period of time to achieve a desired effect. For example, multiple applications can be administered over a treatment period of, for example, about 1 month to about 24 months (e.g., about 3 months, about 6 months, about 9 months, about 12 months, about 15 months, about 18 months, or about 21 months), although longer treatment periods also are contemplated. In some instances, a skin-active agent is administered multiple times per week and/or multiple times a day during the treatment period. For example, a skin-active agent is optionally applied once or twice daily for one or more days per week (e.g., 2, 3, 4, 5, 6, or 7 days per week) for a period of time sufficient to achieve and/or maintain the desired results.

The composition may be applied as part of routine hygiene relating to the skin, hair, and scalp. In one aspect, an agent identified as described herein is formulated as, e.g., shampoo, conditioner, tonic, shower gel, liquid hand cleanser, facial cleanser, moisturizer, lotion (e.g., clarified lotion), skin lotion or cream (such as eye cream and/or lip cream), facial skin cosmetics (such as blusher and highlighter), eye cosmetics (such as eye shadow, eye brow color, and eye liner), lip cosmetics (such as lip rouge), foundation, concealer, wrinkle soothing serum, mascara, skin facial mask, sunscreen, scalp hair styling aid, facial hair styling aid, emulsion, oil, mousse, ointment, milk, pomade, solution, spray, aerosol, powder, foam, gel (such as skin gel, eye gel, and/or lip gel), serum, stick, paste, or other skin and hair products or treatment. In one embodiment, the composition is intended to be left on the skin and/or hair for some esthetic, prophylactic, therapeutic or other benefit (i.e., a "leave-on" composition).

Non-limiting examples of components that can be included in a personal care composition include: conditioning agents, cellulose or guar cationic deposition polymers, natural cationic deposition polymers, synthetic cationic deposition polymers, anti-dandruff agents, gel networks (e.g., fatty alcohol/surfactant networks), particles, suspending agents (such as suspending agents described in, e.g., U.S. Pat. No. 4,741,855 and RE34,584), paraffinic hydrocarbons, propellants, viscosity modifiers, dyes, non-volatile solvents, water soluble diluents, water insoluble diluents, opacifying agents, pearlescent aids, foam boosters, additional surfactants or nonionic cosurfactants, pediculocides, pH adjusting agents, perfumes, preservatives, chelants, proteins, skin active agents, sunscreens, UV absorbers, vitamins, amino acids, mono- or divalent salt, fragrance, skin conditioning agents, exfoliants, and mixtures thereof. Exemplary conditioning agents include, but are not limited to, organic conditioning oils, hydrocarbon oils, polyolefins, fatty esters, fluorinated conditioning compounds, fatty alcohols, alkyl glucosides and alkyl glucoside derivatives, quaternary ammonium compounds, polyethylene glycols, and silicone conditioning agents (e.g., silicone conditioning agents described in U.S. Reissue Pat. No. 34,584; U.S. Pat. Nos. 2,826,551; 3,964,500; 4,364,837; 5,104,646; and 5,106,609; British Patent No. 849,433; and Silicon Compounds, Petrarch Systems, Inc. (1984)). Non-limiting examples of suitable synthetic cationic deposition polymers are described in U.S. Patent Application Publication No. 2003/0223951. Exemplary anti-dandruff additives are described in, e.g., U.S. Pat. Nos. 2,694,668; 2,809,971; 3,152,046; 3,236,733; 3,753,196; 3,761,418; 4,345,080; 4,323,683; 4,379,753; 4,470,982; and 4,885,107. A personal care composition also, in certain embodiments, contains a preservative system to inhibit microbiological growth and maintain the integrity of the product. Exemplary components of personal care compositions also are disclosed in, e.g., U.S. Pat. Nos. 7,772,214; 7,727,516; 7,709,015; 7,704,932; 7,585,827; and 7,531,497. U.S. Pat. Nos. 7,101,889; 5,624,666; 6,451,300, 6,974,569, and 7,001,594 are non-limiting examples of U.S. patents comprising guidance on compositions, formulations, vehicles, administration, and other aspects relating to personal care products comprising anti-dandruff agents formulated for the treatment of dandruff. The entire disclosures of the patents listed herein are incorporated herein by reference, particularly with respect to the teachings relating to formulation of personal care compositions.

EXAMPLES

The invention will be better understood by reference to the following examples which are offered by way of illustration not limitation.

Example 1

This example describes an exemplary method for generating an instance.

Individual experiments (referred to as batches) generally comprise 30 to 96 samples analyzed using Affymetrix GeneChip® technology platforms, containing six replicates of the vehicle control (e.g., DMSO), two replicate samples of a positive control that gives a strong reproducible effect in the cell type used, and samples of the test material/perturbagen. Replication of the test material was performed in separate batches due to batch effects. In vitro testing was performed in 6-well plates to provide sufficient RNA for GeneChip® analysis (2-4 µg total RNA yield/well).

Human telomerized keratinocytes (tKC) were obtained from the University of Texas, Southwestern Medical Center, Dallas, Tex. tKC cells were grown in EpiLife® media with 1× Human Keratinocyte Growth Supplement (Invitrogen, Carlsbad, Calif.) on collagen I coated cell culture flasks and plates (Becton Dickinson, Franklin Lakes, N.J.). Keratinocytes were seeded into 6-well plates at 20,000 cells/cm$^2$ 24 hours before chemical exposure. Human skin fibroblasts (BJ cell line from ATCC, Manassas, Va.) were grown in Eagle's Minimal Essential Medium (ATCC) supplemented with 10% fetal bovine serum (HyClone, Logan, Utah) in normal cell culture flasks and plates (Corning, Lowell, Mass.). BJ fibroblasts were seeded into 6-well plates at 12,000 cells/cm$^2$ 24 hours before chemical exposure.

All cells were incubated at 37° C. in a humidified incubator with 5% $CO_2$. At t=-24 hours cells were trypsinized from T-75 flasks and plated into 6-well plates in basal growth medium. At t=0 media was removed and replaced with an appropriate dosing solution of perturbagen as per the experimental design. Dosing solutions were prepared the previous day in sterile 4 ml Falcon snap cap tubes. Pure test materials may be prepared at a concentration of 1-200 µM, and botanical extracts may be prepared at a concentration of 0.001 to 1% by weight of the dosing solution. After 6 to 24 hours of chemical exposure, cells were viewed and imaged. The wells were examined with a microscope before cell lysis and RNA isolation to evaluate for morphologic evidence of toxicity. If morphological changes were sufficient to suggest cytotoxicity, a lower concentration of the perturbagen was tested. Cells were then lysed with 350 ul/well of RLT buffer containing β-mercaptoethanol (Qiagen, Valencia, Calif.), transferred to a 96-well plate, and stored at -20° C.

RNA from cell culture batches was isolated from the RLT buffer using Agencourt® RNAdvance Tissue-Bind magnetic beads (Beckman Coulter) according to manufacturer's instructions. One microgram of total RNA per sample was labeled using Ambion Message Amp™ II Biotin Enhanced kit (Applied Biosystems Incorporated) according to manufacturer's instructions. The resultant biotin labeled and fragmented RNA was hybridized to an Affymetrix HG-U133A 2.0 GeneChip®, which was then washed, stained and scanned using the protocol provided by Affymetrix.

Example 2

This example describes a method for generating a gene expression signature representative for a plurality of biological conditions. The methodology employed gene expression profiles associated with multiple skin conditions. It will be appreciated, however, that the method is applicable to any combination of biological conditions.

Gene expression datasets for five skin disorders (dandruff, acne, atopic dermatitis, eczema and psoriasis) were collected. Each lesion biopsy was compared to "healthy" biopsy using t-test. One-tailed t-test $p_t$ value was computed for each probe set and was used to calculate a log-odds ratio. The log-odds ratio is a measurement of significance of change and is symmetric for up/down regulated probes. The log-odds ratio was then transformed using a soft threshold function, and the resulting values across all the five skin disorders were used to compute a consistency value using a formula similar to t-statistics. The probes were then ranked based on the computed consistency value. The method is further described in the following paragraphs.

The dandruff dataset was generated internally, while acne, atopic dermatitis, eczema and psoriasis gene expression datasets were obtained from NCBI Gene Expression Omnibus (a repository for gene expression dataset from published literature). The Omnibus data was collected from: Acne, citing Trivedi et al., "Gene array expression profiling in acne lesions reveals marked upregulation of genes involved in inflammation and matrix remodeling," J Invest Dermatol; 126(5):1071-9 (2006); PMID: 16528362); Atopic dermatitis, citing Plager et al., "Early cutaneous gene transcription changes in adult atopic dermatitis and potential clinical implications," Exp Dermatol; 16(1):28-36 (2007); PMID: 17181634, and Plager et al., "Gene transcription changes in asthmatic chronic rhinosinusitis with nasal polyps and comparison to those in atopic dermatitis, PLoS One; 5(7):e11450 (2010); PMID: 20625511), Eczema, citing Olsson et al., "Increased expression of aquaporin 3 in atopic eczema," Allergy; 61(9):1132-7 92006); PMID: 16918518, and Mobini et al., "A module-based analytical strategy to identify novel disease-associated genes shows an inhibitory role for interleukin 7 Receptor in allergic inflammation," BMC Syst Biol; 3:19 (2009); PMID: 19216740), and Psoriasis, citing Nair et al., "Genome-wide scan reveals association of psoriasis with IL-23 and NF-kappaB pathways," Nat Genet; 41(2):199-204(2009); PMID: 19169254, and Swindell et al., "Genome-wide expression profiling of five mouse models identifies similarities and differences with human psoriasis," PLoS One; 6(4):e18266 92011), PMID: 21483750).

Each skin disorder dataset (gene expression profile) was normalized using a standard microarray normalization method. Lesion biopsy samples were compared to "healthy" biopsy samples using one-tailed t-test to derive one-tailed p-value $p_t$ for each probe set. Because the gene expression profiles were not generated using the same microarray chip, only probe sets common to all five gene expression profiles were considered. A log-odds ratio was computed for each probe set for each sample using the formula: lod=log((1-$p_t$)/$p_t$). Each log-odds ratio was transformed using a soft threshold function: c=(1/(1+e$^{-alpha*lod}$))–0.5 to derive value c for each probe set. A parameter alpha was used to control the steepness of the threshold. alpha=1.5 was used in this study.

The c-value for each probe set across the five skin conditions derived as set forth above was used to calculate a one-sample t-test statistic. A small valued 0.01 was added to the sum of square in the t-test formula to avoid division by zero error. One-tailed p-value $p_{t2}$ is calculated and the log-odds ratio was computed using the formula lod=log((1-$p_{t2}$)/$p_{t2}$) for each probe set. The log-odds values computed were sorted in decreasing order. The top ranked probe sets represent the most consistently up-regulated probe sets, and the bottom ranked probe sets represent the most consistently down-regulated probe sets across the skin conditions.

An exemplary unhealthy skin gene expression signature includes the 70 most significant up- and 70 most significant down-regulated genes set forth in Tables A and B, such as a gene expression signature comprise the genes set forth in FIG. 1.

The method described herein can be used to generate a list of genes, the expression of which is consistently altered among a set of biological conditions that is not limited to the conditions described above. The approach used to generate the unhealthy skin gene expression signature can be applied to any data set including, but not limited to, data sets generated from proteomics, metabolomics, and lipidomics experiments.

Example 3

This example illustrates a method for using the unhealthy skin gene expression signature to reliably screen for candidate skin-active agents.

The unhealthy gene expression signature was generated as described above. The signature was used to query a C-Map database comprising gene expression profiles from fibroblast and keratinocyte cell lines exposed to a large number of different agents (i.e., "skin instances"). Many of the agents represented are used to treat skin and other diseases or are used in cosmetic products. Many of agents represented have no history of use in drugs or cosmetic products. Each agent was tested at several concentrations. As shown in Table C, the highest-ranked results (those instances displaying the strongest negative linkage scores) include several instances of estradiol, niacinamide, all-trans retinoic acid, and Olivem 460, all of which are known to have dramatic effects on normalizing aging or damaged skin in vivo. This result validates the effectiveness of the process.

TABLE C

| Chip ID | Chemical | Score | Up Score | Down Score |
|---|---|---|---|---|
| GSS0222_2_11 | Estradiol | −0.925 | −0.666 | 0.259 |
| GSS0222_2_39 | Estradiol | −0.899 | −0.628 | 0.272 |
| GSS0222_2_29 | Estradiol | −0.820 | −0.579 | 0.240 |
| GSS0222_2_46 | Estradiol | −0.769 | −0.571 | 0.198 |
| GSS0222_2_55 | Estradiol | −0.736 | −0.596 | 0.140 |
| GSS0222_2_36 | Estradiol | −0.734 | −0.571 | 0.164 |
| GSS073_9.1 | Nicotinamide | −0.710 | −0.551 | 0.159 |
| GSS0206_32 | Melatonin | −0.684 | −0.422 | 0.262 |
| GSS0206_51 | All-trans retinoic acid | −0.648 | −0.332 | 0.316 |
| GSS0222_2_06 | Estradiol | −0.614 | −0.490 | 0.124 |
| GSS094_estradiol | Estradiol | −0.590 | −0.484 | 0.106 |
| GSS074_15.3 | Nicotinamide | −0.590 | −0.365 | 0.225 |
| GSS0206_43 | Nicotinamide | −0.561 | −0.424 | 0.137 |
| GSS074_15.1 | Nicotinamide | −0.553 | −0.412 | 0.142 |
| GSS0206_19 | Melatonin | −0.530 | −0.380 | 0.151 |
| GSS093_estradiol | Estradiol | −0.529 | −0.410 | 0.119 |
| GSS0222_2_50 | Estradiol | −0.510 | −0.305 | 0.205 |
| GSS0206_52 | Melatonin | −0.468 | −0.212 | 0.256 |

The results shown in Table C also confirm that gene expression profiles from keratinocyte cell lines (a proxy for the epidermis) are useful for screening of candidate agents for cosmetics and/or therapeutic agents to treat a wide variety of disorders of the skin.

This Example illustrates that that connectivity mapping, instances, and gene expression signatures as described herein can be used to reliably screen for candidate skin-active agents for improving skin conditions. The screening can be conducted without understanding the mechanisms of action involved in the particular skin condition of interest.

Example 4

This example demonstrates use of the unhealthy skin gene expression signature to distinguish dandruff suffers from non-dandruff suffers. When treated to resolve dandruff symptoms, subjects exhibit a reversal of the unhealthy skin gene expression signature to that resembling healthy skin.

Figure 9:
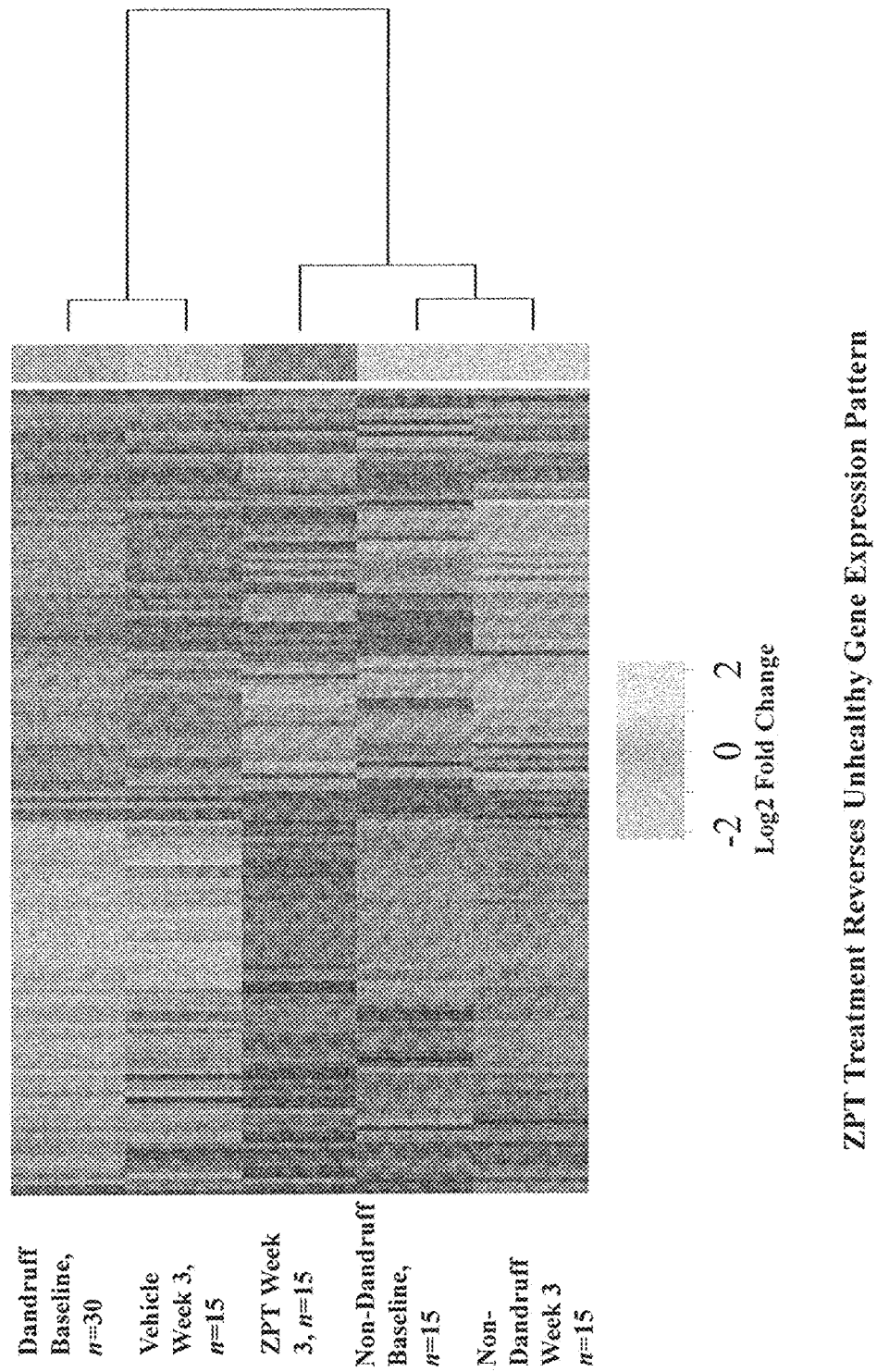
FIG. 9 is a heat map (in grayscale) illustrating the ability of the unhealthy skin gene expression signature to distinguish between dandruff and asymptomatic subjects, and illustrating reversal of the unhealthy skin gene expression signature in dandruff suffers treated with zinc pyrithione, the active ingredient in many anti-dandruff shampoos.

Hierarchical Cluster Analysis of Dandruff vs. Non-Dandruff (Study 1): Genome-wide transcriptional profiles of the dandruff condition and healthy scalp were assessed using RNA extracted from full thickness scalp biopsies. Target cDNA (from extracted mRNA) was hybridized to Affymetrix U133 Plus 2 microarrays containing 54,613 probes; statistical analysis revealed more than 7,000 differentially regulated probe sets, corresponding to 3,757 distinct genes (far in excess of the number expected on the basis of chance alone). Using the top 400 significantly regulated probe sets from the unhealthy skin gene expression signature described above, hierarchical clustering analysis was used to group these genes based on similarity of expression across the samples. A heat map of normalized expression values (based on z-score) of these probe sets is presented in FIG. 9 in grayscale. Each row in FIG. 9 represents a single probe set and each column represents the group average of all subjects (not a single microarray experiment). The expression pattern of these genes is sufficient to effect a complete statistical separation between dandruff-involved (lesional) and non-dandruff scalp skin, indicating that the unhealthy gene expression signature is diagnostic of the condition.

Effect of zinc pyrithione (ZPT) on the Unhealthy Skin Gene Expression Signature in Dandruff Sufferers (Study 2): We examined the effect of ZPT on the transcriptomic profile in dandruff sufferers during a course of treatment known to resolve the key symptoms of the condition (flake and itch) and substantially restore the scalp skin histology and cell surface biomarker profile to a healthy state. In this study, we were able to replicate our key transcriptomic findings from Study 1 in a second study population. It is notable that using the expression levels of the same 400 probe sets in the unhealthy gene expression signature, which all satisfied the p<0.05 criterion, hierarchical cluster analysis again clearly separated Dandruff from Non-dandruff (see All Dandruff Baseline vs. Non-Dandruff Baseline). FIG. 9 demonstrates that the dandruff subjects that received three weeks of treatment with ZPT-containing shampoo displayed a gene expression profile that statistically clusters with the normal subjects at baseline and the normal subjects that received vehicle treatment. The shift in the expression pattern of genes in the unhealthy skin gene expression signature in treated dandruff subjects was accompanied by a reversal of the key symptoms of the condition and a restoration of tissue architecture. This underscores the fundamental importance of the gene products associated with this signature to skin homeostasis. The vehicle treatment did not produce a significant effect on the gene expression profile in either study group after three weeks of controlled application of vehicle three times weekly (a total of 9 exposures).

This Example demonstrates that the unhealthy skin gene expression signature described herein distinguishes the presence and the absence of a biological condition in a subject, particularly, distinguishes dandruff suffers from asymptomatic subjects (non-dandruff). Treatment to alleviate the symptoms of the disorder caused a substantial normalization of the expression profile, while the vehicle treatments caused no significant shift in the profile. Thus, the invention provides a method whereby a potential therapeutic could be evaluated in vivo with respect to its effect on gene expression associated with the unhealthy skin signature. In this regard, a positive biological effect can be defined, at least in part, by the reversal of the expression pattern of genes that reside within this signature.

Example 5

This example illustrates methods for characterizing perturbagen activity in models of skin conditions. In particular, the example describes exemplary inflammation, cell proliferation, cell differentiation, and lipid metabolism assays.

Lipid Metabolism Assay

All assays may be performed using HEKn cells. HEKn cells are cultured in keratinocyte growth media (Epi-Life media (Cascade, catalog no. M-EPI-500-CA)) supplemented with Human Keratinocyte Growth Supplement (HKGS) (Cascade, catalog no. S-001-5). The cells are seeded on 60 mm dishes resulting in 70,000 cells per plate. When the plates are 90%-100% confluent, the keratinocyte growth media is replaced with DMEM: Hams F-12 (2:1) (DMEM (Gibco, catalog no. 21068), Hams F12 (Gibco, catalog no. 11765) (2:1), 10% Fetal Bovine Serum (Gibco, catalog no. 10437-077); 10 µg/ml Insulin (Gibco, catalog no. 12585-014); 0.4 µg/ml hydrocortisone (Sigma, catalog no. H0135); and 1% CD lipid concentrate (Gibco, catalog no. 11905).

When 90-100% confluency is observed, HEKn cells are exposed to a perturbagen or calcium for 10 days with media changes every 48 hrs. Cells are examined daily under a microscope. At day 10, the plates are rinsed with phosphate buffered saline three times (1×PBS (Media Tech, Cellgro #21-040-CV)), and 200 µl of 2% SDS/300 mM Urea is added to each plate. The plates are scraped, two plates of the same treatment are pooled, and resulting lysates are stored at −80° C.

To extract lipid from the cells, the lysates are thawed and approximately 160 ml of lysate is mixed with 1 ml of nanopure water. Three milliliters of 1:2 chloroform:methanol is added and mixed. An additional milliliter of chloroform is added, the mixture is vortexed for one minute to achieve phase separation. The mixture is centrifuged at 2500 rpm for 10 minutes. The chloroform (bottom) layer is removed and transferred to a clean test tube. To the chloroform layer is added 4 ml 10:10:9 chloroform:methanol:water, and the mixture is vortexed for 30 seconds, and again centrifuged at 2500 rpm for 10 minutes. The chloroform layer is removed and transferred to a Reacti-vial, and evaporated to dryness under nitrogen. All samples are stored at −80° C.

Thin layer chromatography (TLC) is employed to separate lipids. Dried samples are reconstituted in 100 µl of 2:1 chloroform:methanol and quickly transferred to TLC vials. Samples are spotted on TLC plates. An AMD 2 System with winCATS may be employed using the following solvents: chloroform (Burdick & Jackson, catalog no. #048-4), acetone (Burdick & Jackson, catalog no. #AX0015-1), methanol (Burdick & Jackson, catalog no. #AX230-4), ethyl ether (Burdick & Jackson, catalog no. #AH106-4), and ethyl acetate (Aldrich, catalog no. #319902)+5% Acetic Acid (Sigma Aldrich, catalog no. #242853). After separation, the plates are dried, sprayed with sulfuric acid, charred on a hot plate for about 45 minutes, cooled, then scanned. Free fatty acid, ceramide, and cholesterol from the samples are quantified, and the lipid levels of perturbagen-treated cells are compared to lipid levels in calcium-treated cells.

Cell Differentiation Assay

Cell differentiation may be evaluated by detecting cornified envelope development. Cells are cultured as described above with respect to the lipid metabolism assay. When 90-100% confluency is observed, HEKn cells are exposed to a perturbagen or Anthralin for 6 days with media changes every 48 hours. Cells are examined daily under a microscope. At day 6, the plates are rinsed with phosphate buffered saline three times (1×PBS (Media Tech, Cellgro #21-040-CV)), and 200 μl of 2% SDS/300 mM urea is added to each plate. The plates are scraped, two plates of the same treatment are pooled, and resulting lysates are stored at −80° C.

To determine total protein concentration, cells are thawed on ice and sonicated. The lysate is boiled for 10 minutes, and 40 μl is removed for protein measurement ("protein sample"). The protein sample is diluted 1:2 in 2% SDS/300 mM urea buffer, and returned to −80° C. The protein samples are thawed and diluted 1:2 (40 μl) in 2% SDS/300 mM urea buffer. Total protein is measured using the Pierce BCA Protein Assay Kit (Pierce, catalog no. 23225) following the manufacturer's instructions.

To measure cross-linked envelope protein, lysates are centrifuged at 13,000 rpm for 15 minutes to remove soluble protein. The supernatant is removed, and 500 μl of fresh 2% SDS is added, the mixture is vortexed, and then centrifuged at 13,000 rpm for another 15 minutes. The supernatant is removed, 500 μl of fresh 2% SDS is added, the mixture is vortexed, and then centrifuged at 13,000 rpm for 15 minutes. The supernatant is removed. The resulting pellet is resuspended in 300 μl of 2% SDS and vortexed. A 100 μl aliquot of the sample is transferred into a clear 96-well plate and absorbance is measured (OD at 340 nM) to quantify cross-linked envelope protein. The absorbance readings are normalized to readings of the BCA total protein sample. The level of cross-linked envelope protein of perturbagen-treated cells is compared cross-linked envelope protein levels in Anthralin-treated cells.

Inflammation Assay

Human Tert cells are cultured in complete media (Eppilife Media (Invitrogen, catalog no. M-EPI-500-CA)) supplemented with HKGS (Invitrogen, catalog no. S-001-5) and AB/AM (Invitrogen, catalog no. R-015-10). Media is changed every 48 hours. Cells are seeded (25,000 cells/plate) onto a 24 well plate and incubated overnight at 37° C. to allow attachment. The following day, the complete media is removed and replaced with modified media that that does not contain BPE, hEGF and antibiotic—Eppilife Media (Invitrogen, catalog no. M-EPI-500-CA) supplemented with insulin, hydrocortisone, and transferrin of the HKGS kit (Invitrogen, catalog no. S-001-k). The cells are allowed to incubate overnight.

If desired, multiple concentrations of perturbagen are assayed simultaneously (e.g., 0.5 μM and 1 μM). The following treatment parameters are merely exemplary and may be modified to adjust for culture plate size, number of perturbagens tested simultaneously, activity of the perturbagens, and the like. The media is removed by vacuum and 1 mL of one of the following is applied to each well: (a) modified media comprising DMSO and lacking cytokines, (b) modified media comprising DMSO and cytokines (human IL-22 (20 ng/mL (R&D, catalog no. 782-IL) and human IL-17a (200 ng/mL (R&D, catalog no. 314-ILB)); (c) modified media comprising cytokines, DMSO, and clobetasol; (c) modified media comprising cytokines, DMSO, and 50 μM perturbagen; and (d) modified media comprising cytokines, DMSO, and 100 μM perturbagen. Clobetasol is a corticosteroid which blocks IL-8 production and, therefore, is a useful benchmark in the context of the inflammation assay. Clobetasol is commonly prescribed to treat eczema, psoriasis, and contact dermatitis.

A sample of media (100 μL) is collected at 48 hours following treatment to examine IL-8 levels, which is surrogate for the inflammatory cascade. ATP levels are measured using the CellTitler-Glo® Luminescent Cell Viability Assay (Promega), which determines the number of viable cells in culture based on quantitation of the ATP present. IL-8 in the media samples is analyzed using Luminex Technology available from Millipore. The amount of IL-8 (pg/mL) is normalized to the ATP signal. The level of IL-8 production in cells treated with perturbagen is compared to the level of IL-8 production in cells treated with clobetasol. While the methods are described with respect to keratinocytes growing in monolayer culture, the assay framework can be applied to both three-dimensional organotypic cultures and ex vivo human skin cultures.

Cell Proliferation Assay

The following methodology is described in terms of three-dimensional organotypic cultures; however, the method also may be applied to monolayer cultures or ex vivo skin explants. Human three-dimensional organotypic cultures are exposed to a perturbagen or clobetasol for about 96 hours. The cultures are labeled with a six hour pulse of BrdU (Sigma, St. Louis, Mo., USA) at a final concentration of 10 μM. Immunohistochemical staining is performed on paraffin-embedded tissues sectioned at 8 μM thickness using monoclonal antibodies against BrdU (Roche, Indianapolis, Id., USA) and Vectastain ABC (peroxidase) kit (Vector Labs, Burlingame, Calif., USA). The number of BrdU-positive cells is determined and expressed as a percentage of total cells in the basal layer (labeling index ("LI")). Perturbagens are evaluated on the basis of their effect on the LI, in the absence of overt cytotoxicity. Cellular proliferation in cultures treated with perturbagen is compared to cellular proliferation in cultures treated with clobetasol.

The assays describe herein are representative of the physiological themes common in a number of skin disorders and implicated in the unhealthy skin gene expression signature described herein. The effect of perturbagens on skin homeostasis and skin disorders can be further characterized using any one or more of the assays.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. In particular, this application claims the benefit of U.S. Provisional Application No. 61/683,667, which is incorporated herein by reference in its entirety. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for evaluating the influence of a perturbagen on skin homeostasis and formulating a skin care composition comprising the perturbagen, the method comprising:
   causing a computer processor to query a data architecture of stored skin instances, each skin instance being associated with a perturbagen, with an unhealthy skin gene expression signature, wherein the query comprises comparing the unhealthy skin gene expression signature to each stored skin instance and assigning a connectivity score to each instance, and wherein constructing the unhealthy skin gene expression signature comprises
      (a) obtaining gene expression measurements for a plurality of skin conditions,
      (b) identifying genes differentially expressed in the skin conditions by comparing the gene expression measurements of (a) with gene expression measurements for a control sample,
      (c) causing a computer processor to calculate a gene expression consistency value by
         (i) computing a log-odds ratios for the differentially expressed genes,
         (ii) transforming the log-odds ratios using a sigmoid function,
         (iii) performing a one-tailed t-test against zero, and
         (iv) computing a log-odds ratio from the one-tailed t-test to achieve a gene expression consistency value,
      (d) creating an ordered list comprising identifiers representing the consistently differentially expressed genes, wherein the identifiers are ordered according to the gene expression consistency value computed in (c), and
      (e) storing the gene expression signature list on at least one non-transitory computer readable medium; and
   identifying a skin instance having a negative connectivity score;
   identifying at least one perturbagen associated with the skin instance having the negative connectivity score; and
   combining the at least one perturbagen with a dermatologically acceptable carrier to form a skin care composition.

2. The method according to claim 1, wherein the unhealthy skin gene expression signature comprises between about 5 and about 400 up-regulated genes, and between about 5 and about 400 down-regulated genes.

3. The method according to claim 1, wherein the unhealthy skin gene expression signature comprises at least one up-regulated gene selected from the group consisting of TSTA3, ARPC5L, SYNCRIP, PPP4R1, POL3S, TUBB6, CCT5, GALNT6, C12orf5, S100A11P, TNIP2, D1MT1L, OTUB1, MPZL2, DDX39, EIF6, PLSCR3, LAPTM5, MPZL2, SAMSN1, SLC43A3, ZWINT, EHBP1L1, TRIM14, HNRNPA2B1, TNIP2, EBNA1BP2, SECTM1, FAIM3, N4BP1, N4BP1, SNRPD3, LAPTM5, LOC391020, TRABD, C20orf11, and 216952_s_at.

4. The method according to claim 3, wherein the unhealthy skin gene expression signature comprises at least one up-regulated gene selected from the group consisting TSTA3, ARPC5L, SYNCRIP, PPP4R1, POL3S, TUBB6, CCT5, GALNT6, C12orf5, S100A11P, and TN1P2.

5. The method according to claim 1, wherein the unhealthy skin gene expression signature comprises at least one down-regulated gene selected from the group consisting of LMOD1, C14orf132, GPD1L, TRIM2, RNF38, LONP2, 222362_at, PHYHIP, FAM117A, RHOBTB3, NUAK1, CHP2, CREBL2, RAI2, FXYD6, MID2, CCNI, PELI2, FOXJ3, ANKRD25, IAA0265, FLJ10357, OSBPLIA, DDX42, C1orf115, C21orf25, TTC3, RPS14, 212498_at, PFAAP5, TSPYL5212970_at, C6orf48, IHPK2, and RP4-691N24.1.

6. The method according to claim 5, wherein the unhealthy skin gene expression signature comprises at least one down-regulated gene selected from the group consisting of PHYHIP, FAM117A, PHOBTB3, CHP2, C1.4orf132, LONP2, 222362_at, CCNI, PELI2, LMOD1, GPD1L, TRIM2, CREBL2, RAI2, FXYD6, MID2, FOXJ3, and ANKRD25.

7. The method according to claim 1, wherein the unhealthy skin gene expression signature comprises between about 80% and about 100% of the up-regulated genes set forth in Table A and between about 80% and about 100% of the down-regulated genes set forth in Table B.

8. The method according to claim 1, wherein the unhealthy gene expression signature comprises between about 80% and about 100% of the genes set forth in Table C.

9. The method according to claim 1, wherein the connectivity score has a value between +2 and −2.

10. The method according to claim 1, further comprising characterizing activity of a perturbagen associated with a skin instance by exposing a human skin cell to the perturbagen in one or more assays selected from the group consisting of an inflammation assay, an epidermal differentiation assay, an epithelial cell proliferation assay, and a lipid metabolism assay.

11. The method according to claim 10, further comprising characterizing activity of the perturbagen in an ex vivo skin model of inflammation.

12. The method of claim 11, wherein the ex vivo model of skin inflammation comprises a mammalian skin sample comprising an epidermal layer and a dermal layer, wherein inflammation is induced by delivering an effective amount of a stimulant selected from the group consisting of IL-17, IL-22, IL-1b, and combinations thereof, to the mammalian skin sample.

13. The method according to claim 10, further comprising characterizing activity of the perturbagen in a three-dimensional organotypic model of inflammation.

14. The method according to claim 1, wherein the method further comprises (a) characterizing the activity of the perturbagen in a cell-based assay, (b) characterizing the activity of the perturbagen in an ex-vivo tissue assay, and (c) characterizing the activity of the perturbagen in vivo.

15. The method according to claim 1, wherein (a) comprises characterizing the activity of the perturbagen in an inflammation assay, an epidermal differentiation assay, an epithelial cell proliferation assay, and lipid metabolism assay; and (b) comprises characterizing the activity of the perturbagen in an ex-vivo skin model of inflammation and/or a three-dimensional organotypic model of inflammation.

16. The method according to claim 1, wherein method the stored skin instances are associated with perturbagens that influence cell signaling, system development, epidermis development, immune system process, and inflammation.

* * * * *